United States Patent
Mide et al.

(10) Patent No.: US 12,268,370 B2
(45) Date of Patent: Apr. 8, 2025

(54) SAMPLE COLLECTION DEVICES

(71) Applicant: ConceptoMed AS, Ballstad (NO)

(72) Inventors: Christian Mide, Ballstad (NO); Jimmy Gidö Schön, Ballstad (NO)

(73) Assignee: CONCEPTOMED AS, Ballstad (NO)

( * ) Notice: Subject to any disclaimer, the term of this patent is extended or adjusted under 35 U.S.C. 154(b) by 897 days.

(21) Appl. No.: 17/116,584

(22) Filed: Dec. 9, 2020

(65) Prior Publication Data

US 2022/0071604 A1 Mar. 10, 2022

(30) Foreign Application Priority Data

Sep. 4, 2020 (GB) .................................... 2013960
Oct. 2, 2020 (GB) .................................... 2015657

(51) Int. Cl.
*A61B 10/00* (2006.01)
*A61B 90/00* (2016.01)

(52) U.S. Cl.
CPC .......... *A61B 10/0051* (2013.01); *A61B 90/08* (2016.02); *A61B 2090/063* (2016.02); *A61B 2090/0807* (2016.02); *A61B 2560/04* (2013.01)

(58) Field of Classification Search
CPC ............ A61B 10/0045; A61B 10/0051; A61B 5/1405; A61B 5/14507; A61M 2202/0466; A61M 2205/071; A61M 2205/076; A61M 2205/11; A61M 2202/04; C12M 33/00
See application file for complete search history.

(56) References Cited

U.S. PATENT DOCUMENTS

| | | | |
|---|---|---|---|
| 9,498,191 B2 | 11/2016 | Granger | |
| 2004/0022687 A1* | 2/2004 | Wuske | A61B 10/0051 422/400 |
| 2004/0210200 A1* | 10/2004 | Gerondale | A61M 5/3158 604/224 |

(Continued)

FOREIGN PATENT DOCUMENTS

| | | |
|---|---|---|
| CN | 110840492 A | 2/2020 |
| DE | 102006052982 A1 | 5/2008 |

(Continued)

OTHER PUBLICATIONS

B. Braun Medical, "Injekt Solo", https://www.bbraun.co.uk/en/products/b/injekt-solo.html.

(Continued)

*Primary Examiner* — Daniel L Cerioni
*Assistant Examiner* — Abel Seifu Abegaz
(74) *Attorney, Agent, or Firm* — Getz Balich LLC

(57) ABSTRACT

A sample collection device for collecting a fluid sample is provided. The device includes a sample collection chamber, for collecting a sample therein, having a first end and a second end and a sample collection conduit, for conveying a sample from a user into the sample collection chamber. The sample collection conduit includes an inlet for receiving a sample and wherein in at least a first position the sample collection conduit extends from within the sample collection chamber out through the first end such that at least the inlet is outside of the sample collection chamber. The device further includes a plunger configured to expel the sample out of the sample collection chamber through the second end of the sample collection chamber.

20 Claims, 27 Drawing Sheets

(56) References Cited

U.S. PATENT DOCUMENTS

| | | | |
|---|---|---|---|
| 2005/0096563 A1 | 5/2005 | Greg | |
| 2006/0057027 A1 | 3/2006 | Hudak | |
| 2008/0058677 A1 | 3/2008 | Yong | |
| 2009/0024060 A1* | 1/2009 | Darrigrand | A61B 10/0051 |
| | | | 600/584 |
| 2011/0020195 A1* | 1/2011 | Luotola | A61B 5/150351 |
| | | | 206/569 |
| 2021/0215585 A1* | 7/2021 | Fruchter | A61B 10/0051 |
| 2022/0071604 A1 | 3/2022 | Mide | |

FOREIGN PATENT DOCUMENTS

| | | | |
|---|---|---|---|
| EP | 520408 A2 * | 12/1992 | A61B 10/0045 |
| EP | 2113203 A1 | 11/2009 | |
| WO | 2018158768 A1 | 9/2018 | |
| WO | 2018201209 A1 | 11/2018 | |

OTHER PUBLICATIONS

DNA Genotek, "DNA from Saliva", 2012, https://www.dnagenotek.com/US/pdf/PD-BR-00048.pdf.
Salimetrics, "Saliva Collection Aid (SCA)", 2021, https://salimetrics.com/product/saliva-collection-aid-sca-50pk/.
Vault Health, "COVID-19 Test Kit", 2021, https://www.vaulthealth.com/covid.
International Search Report for PCT/EP21/74513 dated Dec. 2, 2021.
Sfrintzeris et al. "Struggling to get test equipment for saliva samples", https://www.vg.no/nyheter/innenriks/i/Wb9xMK/sliter-med-aa-faa-tak-i-testutstyr-til-spyttproever, Aug. 28, 2020.
Search and examination report for GB2015657.6 dated Mar. 5, 2021.

* cited by examiner

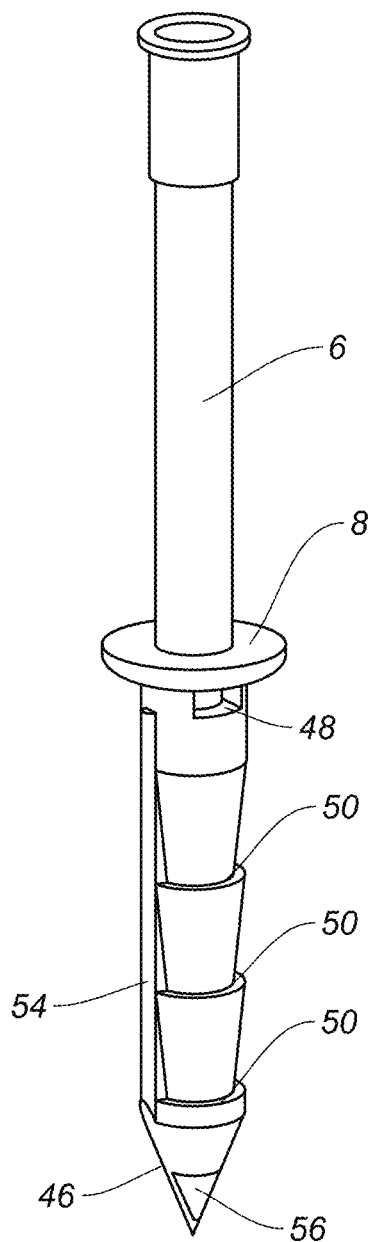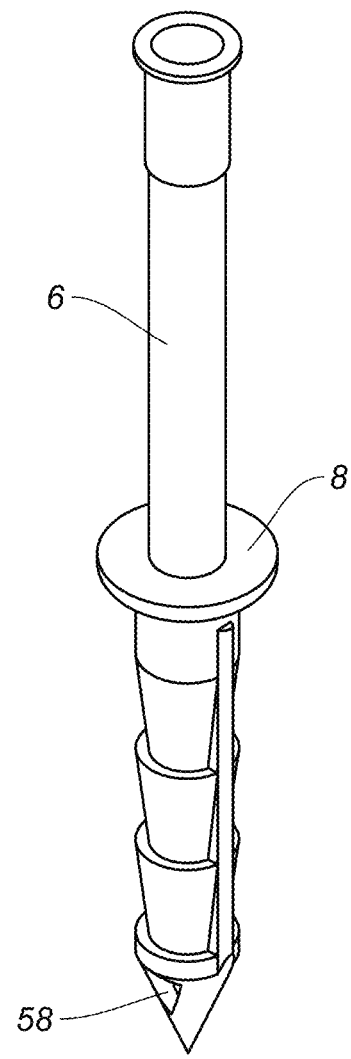
FIG. 4A
FIG. 4B

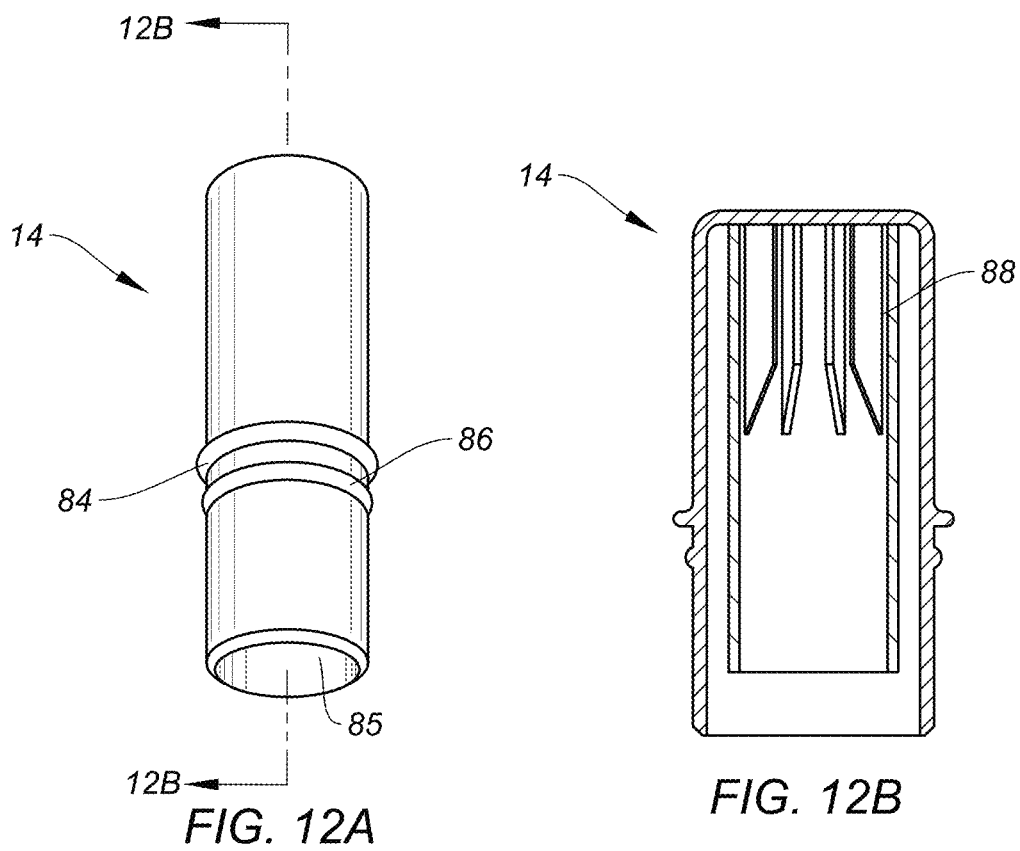
FIG. 12A
FIG. 12B
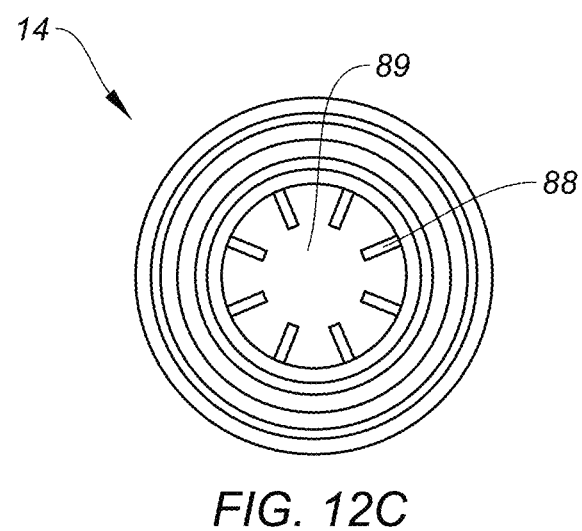
FIG. 12C

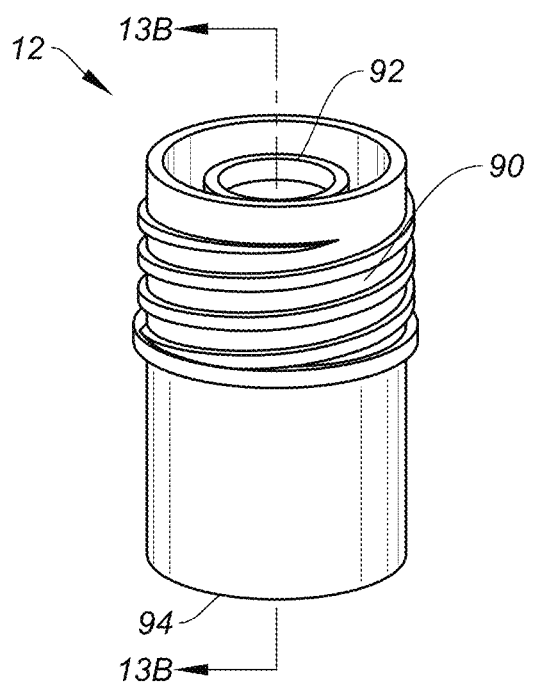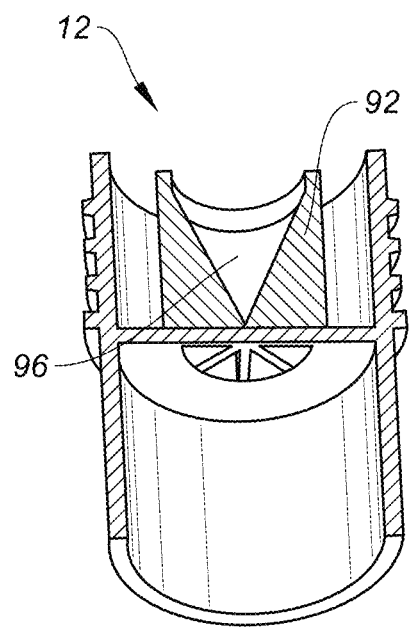
FIG. 13A
FIG. 13B

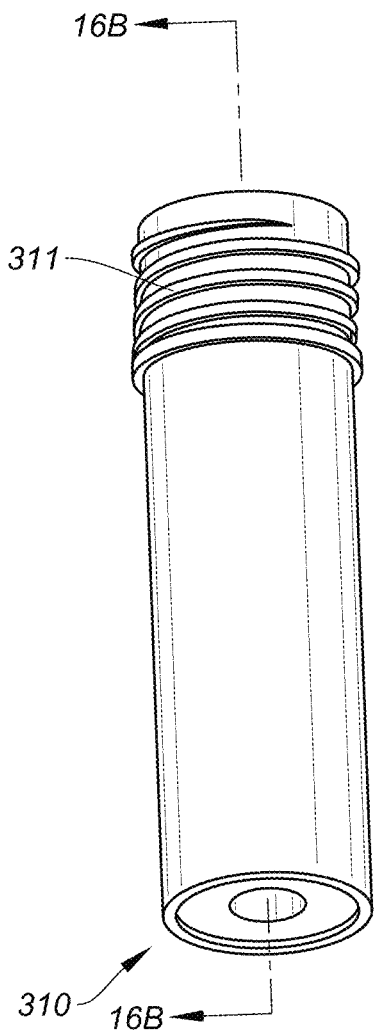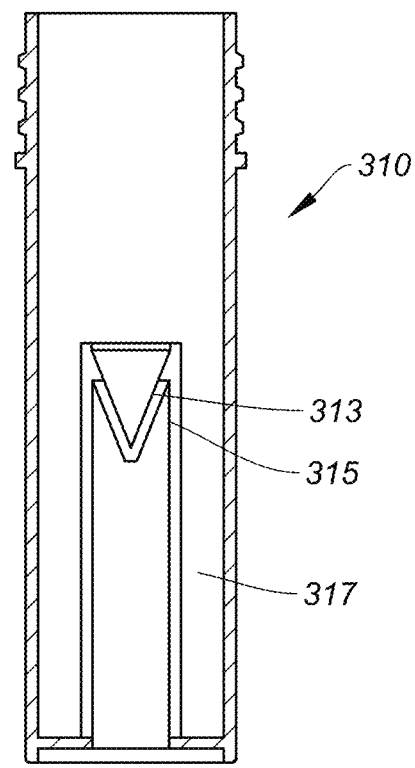
FIG. 16A
FIG. 16B

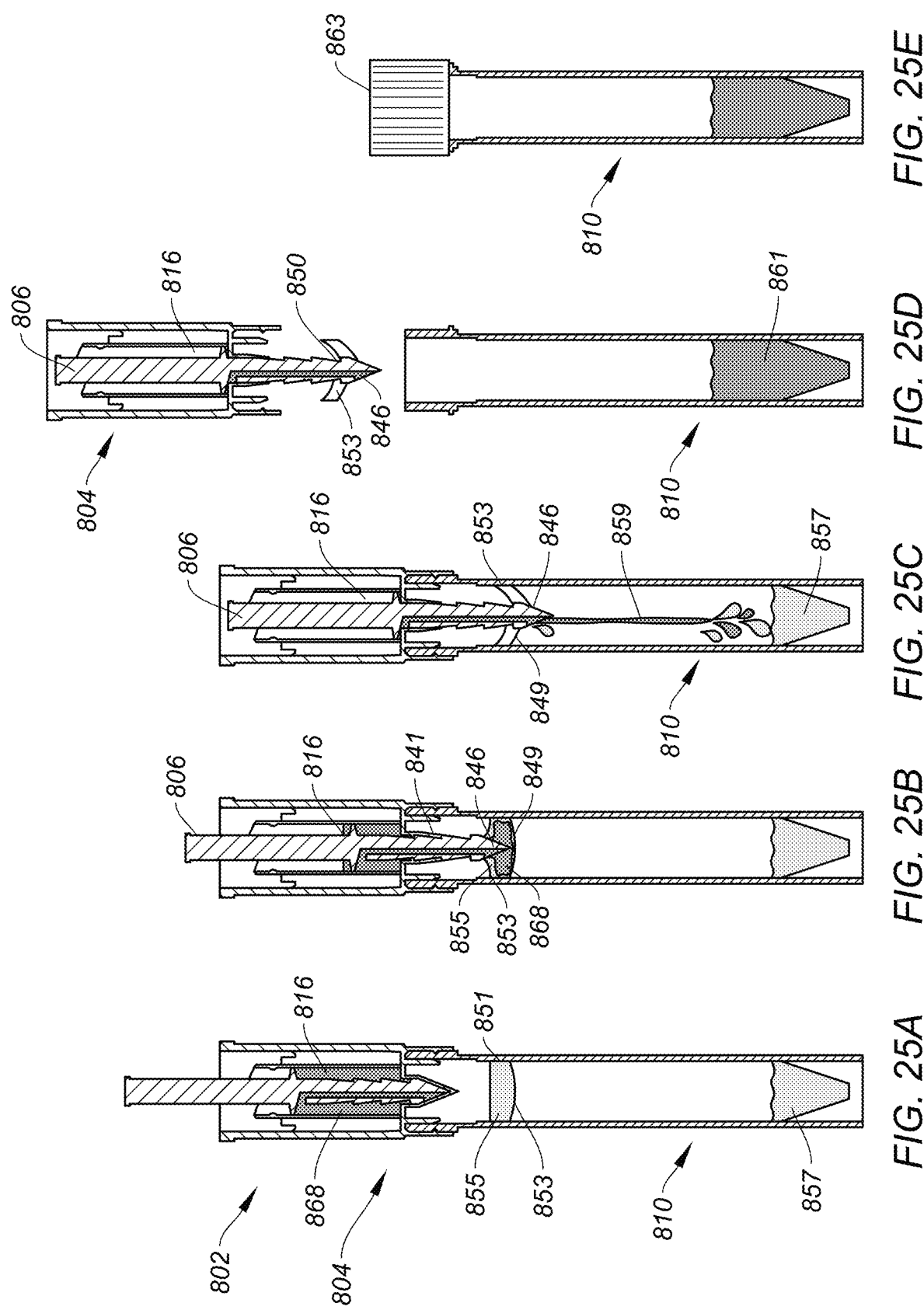

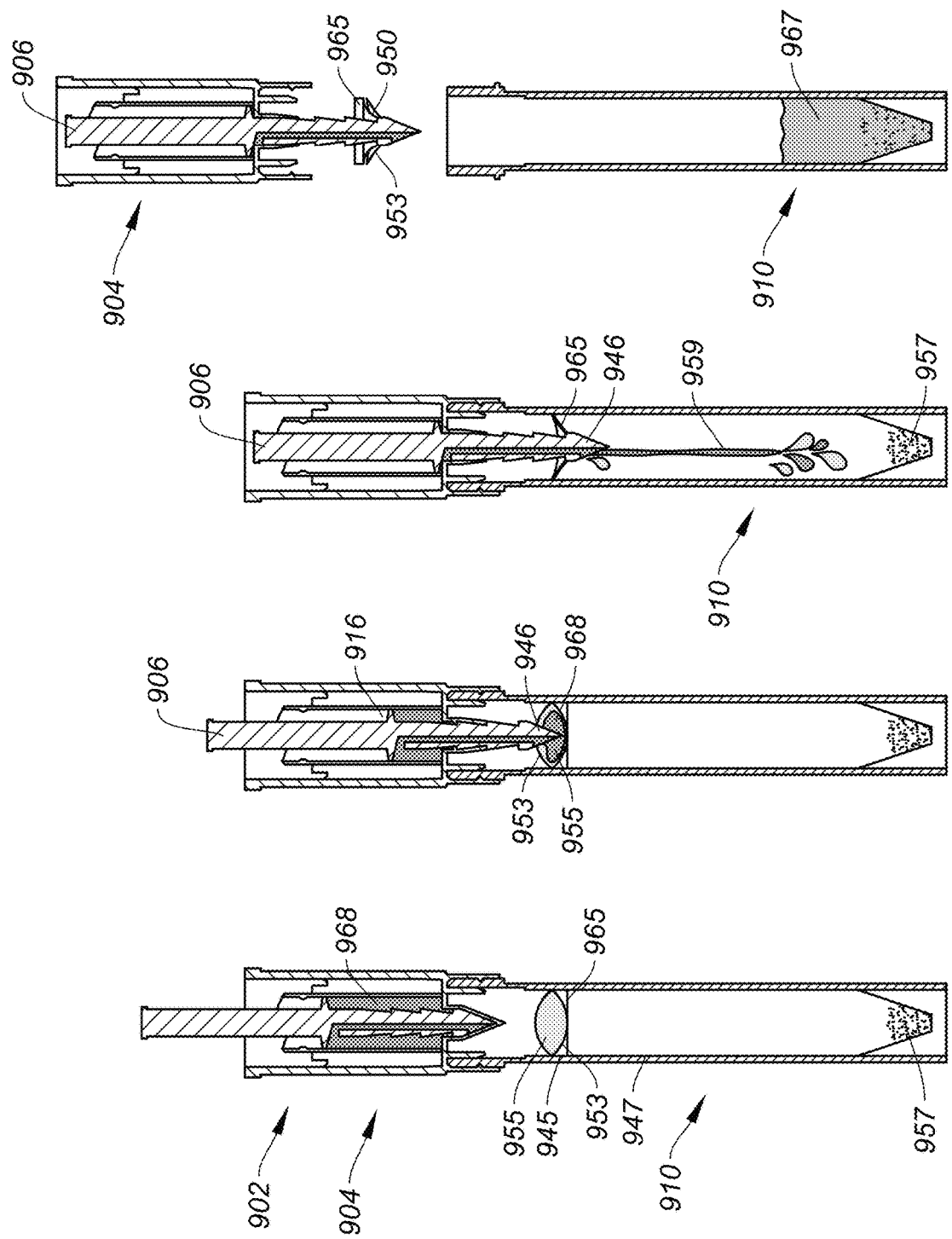

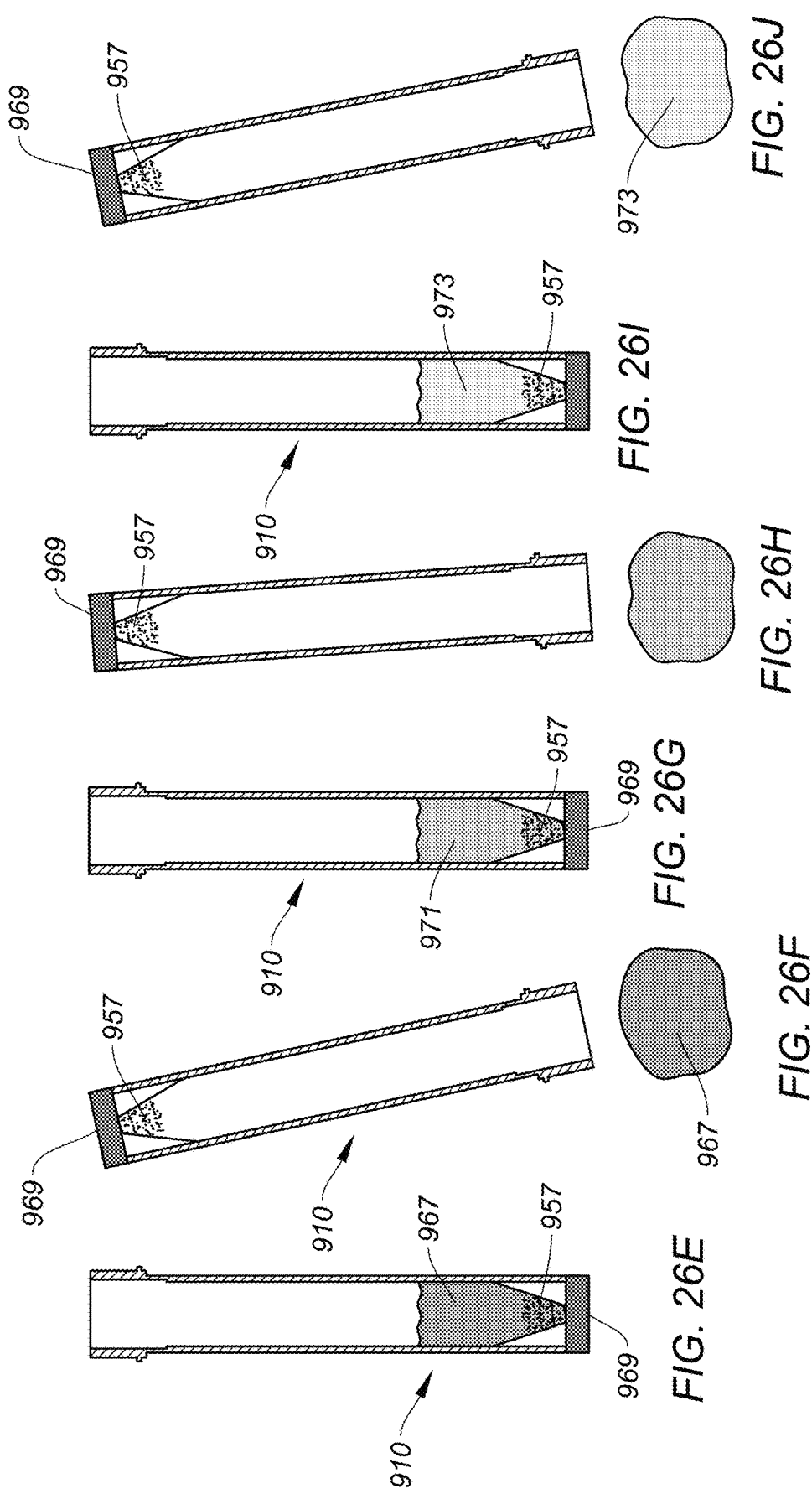

SAMPLE COLLECTION DEVICES

This application claims priority to GB Patent Appln. No. 2013960.6 filed Sep. 4, 2020 and GB Patent Appln. No. 2015657.6 filed Oct. 2, 2020, which are hereby incorporated herein by reference in their entireties.

BACKGROUND OF THE INVENTION

1. Technical Field

The present invention relates to sample collection devices for use in collecting fluid samples, for example oral fluid samples.

2. Background Information

Oral fluid samples, for example fluid samples comprising human saliva, can be analyzed to determine the makeup of the sample. In recent developments, human saliva may be used to determine whether a provider of the sample is infected with a virus, for example severe acute respiratory syndrome coronavirus 2 (SARS-CoV-2) which may indicate that the provider of the sample has coronavirus disease (COVID-19). The testing of oral fluid samples to determine whether a provider of the sample has SARS-CoV-2 may provide an improved means for testing for the virus when compared to other prior art techniques. Prior art techniques for testing include the use of swabs, which are relatively invasive and can in some instances be uncomfortable for the provider of the sample.

The analysis of an oral fluid sample typically requires a relatively precise amount of sample in order for reliable analysis. In order to acquire a precise volume of sample, prior art techniques typically involve the use of a saliva sample kit. Such a kit often includes a number of parts, for example seven different separate components, for use in collecting and measuring a sample. Such kits normally require a user to spit or drool into a funnel which is attached to a measurement vial. The measured saliva is then poured into a secondary vial, and a lid is sealed onto both the measurement vial and the secondary vial. Use of these prior art kits presents a significant risk of contamination of a sample, particularly as the sample is transferred from one container to the other. Further, in the act spitting or drooling into the measurement vial, and subsequent transferring of the sample to the secondary vial, there is a significant risk of inadvertently leaking the sample onto vial threads and other surfaces, such as a work surface, or a user's hands. As the sample may be infected, this therefore increases the risk of infecting others which is clearly not ideal. Furthermore, the amount of oral fluid has been shown to vary substantially when collected by the individual on its own, affecting reproducibility and confidence in the results of such analyses.

Accordingly, while efforts have been made to collect and measure an oral fluid sample for analysis, the prior art devices and techniques clearly have significant limitations and pose potential risks.

SUMMARY OF THE INVENTION

The present invention aims to address, or at least mitigate, one or more of the problems outlined above and when viewed from a first aspect provides a sample collection device, for collecting a fluid sample, comprising: a sample collection chamber, for collecting a sample therein, having a first end and a second end; a sample collection conduit, for conveying a sample from a user into the sample collection chamber, wherein the sample collection conduit comprises an inlet for receiving a sample and wherein in at least a first position the sample collection conduit extends from within the sample collection chamber out through the first end such that at least the inlet is outside of the sample collection chamber; and a plunger configured to expel the sample out of the sample collection chamber through the second end of the sample collection chamber.

Accordingly, as will be appreciated by those skilled in the art, through the use of the sample collection conduit, a user may collect their own fluid sample without requiring assistance from others, e.g. healthcare personnel. The fluid sample collection device may be suitable for collecting any fluid sample, however the sample collection device may be used for collecting an oral fluid sample, e.g. comprising saliva. Given that the sample may, in some instances, be infected with bacteria or a virus, by collecting the sample themselves, the chance of healthcare personnel coming into contact with the potentially infected sample is minimized. By reducing the number of interactions of healthcare personnel with potentially infected persons, this may also reduce the consumption of personal protective equipment (PPE), such as gloves, masks, aprons, etc, which healthcare personnel often have to change frequently, when collecting samples. Further, the lack of need for assistance during sampling and further processing may also substantially reduce costs and resources, e.g. of healthcare personnel, associated with collecting and analyzing samples.

Further, through the use of a sample collection conduit which conveys the sample directly into the sample collection chamber, the sample may be kept isolated from the environment thereby minimizing the chance of the sample becoming contaminated. This may help to ensure that any analysis performed on the sample accurately reflects the sample of the provider, without contamination from others. Additionally, by collecting the sample using the sample collection conduit, the provider of the sample is less likely to get the sample over their hands, which reduces the likelihood of the provider going on to inadvertently deposit their sample on other surfaces.

Use of the device may involve a user placing their mouth around the inlet of the sample collection conduit. The user may then transfer a sample, e.g. comprising saliva, through the sample collection conduit into the sample collection chamber. Transferring of the sample may be achieved by the user applying a spitting action into the sample collection conduit. This may have to be repeated a plurality of times, often up to and above 10 times, to achieve the sufficient volume. Once the sample collection chamber contains a sufficient volume of the sample, the sample may be controllably expelled from the sample collection chamber using the plunger. This may be performed immediately after providing the sample, or the sample may be temporarily stored within the sample collection chamber before it is expelled. The sample may be expelled into or onto in any suitable means, e.g. a means for testing. As will be appreciated, fluid such as the sample, or air subsequently blown by the user to flush the sample collection conduit of any remaining sample therein, may pass through the sample collection conduit into the sample collection chamber.

In order to allow the sample to be expelled from the second end of the sample collection chamber, the second end of the sample collection chamber may comprise an opening through which the sample may pass. The opening may, at least initially, be closed, such that the sample initially collects within the sample collection chamber. The opening may be selectively opened when it is desired to expel the sample.

The sample collection device may allow a user to measure the volume of sample provided. As discussed above, this may be important, as certain types of analysis require a specific volume of sample in order for the analysis to function properly and produce accurate results. Measurement of the sample may be achieved in any suitable means. For example, the sample collection chamber may be dimensioned such that when it is full it contains the correct amount of sample required for optimal analysis. The sample collection chamber may thus be a sample measurement chamber. Accordingly, in this case, the user may simply provide their sample until the sample collection chamber is full, and then stop. The sample collection chamber, and indeed other parts of the device, may be made from a transparent material such that the user can see the sample within the device.

However, in a set of embodiments, the sample collection chamber comprises at least one volumetric marking. The at least one volumetric marking may allow a user to more accurately measure their sample as it fills the sample collection chamber. It may also mean that the device can be used to collect different volumes, depending on the purpose of the sample. The at least one volumetric marking may comprise a plurality of volumetric markings. For example, the markings may include a minimum volume, a target volume, and a maximum volume markings. Such markings may allow a user to aim to provide the target volume of sample. In the exemplary case of testing for SARS-CoV-2, a minimum volume marking may correspond to 0.5 ml, a target volume marking may correspond to 1 ml and a maximum volume marking may correspond to 1.5 ml.

The plunger and the sample collection conduit may be provided by separate parts which may be free to move within the sample collection chamber independently. In a set of embodiments, the sample collection conduit and plunger are operatively linked such that movement of the sample collection conduit causes movement of the plunger. Operatively linking, i.e. coupling, the movement of sample collection conduit and the plunger in this manner may advantageously mean that the sample collection conduit can be used to drive movement of the plunger within the sample collection chamber. This may provide a convenient means for operation of the device. The operative link may be achieved in any suitable manner. For example, the sample collection conduit may act upon the plunger, in order to drive its movement.

In a set of embodiments, however, the sample collection conduit and the plunger are integrally formed. For example, the plunger may be formed in, or on, a wall of the sample collection conduit. This wall could be a base wall or a side wall of the sample collection conduit. For example, the plunger may surround the sample collection conduit, which may be cylindrical. The plunger may be arranged part way along the length of the sample collection conduit such that the sample collection conduit extends above and below the plunger. The sample collection conduit and the plunger may be integrally formed as a single component by any suitable means, for example by integrally forming the parts together in a single mold. In such an embodiment, the movement of the plunger will be inherently coupled to the movement of the sample collection conduit. By integrally forming the sample collection conduit and plunger as a single part, the number of separately operable components on the device may be reduced, and thus the use of the device may be simplified for a user. Further, the manufacture may be simplified, and the cost of manufacture may also be reduced.

In embodiments wherein the movement of the sample collection conduit and plunger is operatively linked, i.e. coupled, the sample collection conduit may be configured to be pushed into the device by a user. This may, for example, comprise the user pushing the sample collection conduit into the sample collection device using their hand, e.g. a thumb, or by pushing the sample collection conduit against another surface. This may therefore advance the sample collection conduit and the plunger into the sample collection chamber. Alternatively, the sample collection conduit may be configured to be rotated in order to advance the sample collection conduit and plunger into the device. For example, the sample collection conduit, or a part thereof such as the plunger, may comprise a threaded portion configured to engage with a corresponding threaded portion on the sample collection chamber. Accordingly, in such embodiments, rotation of the sample collection conduit relative to the sample collection chamber results in the sample collection conduit and plunger advancing into the sample collection chamber. Such an embodiment may allow for more control over the advancement of the plunger and thus more control over the expelling of the sample from the sample collection chamber.

The second end of the sample collection chamber may be closed by a suitable means such that the sample cannot be expelled from the sample collection chamber, by operation of the plunger, until the user chooses to do so. For example, the second end may be closed by a cap which can be selectively removed in order to allow for the sample to be expelled through the second end. However, in a set of embodiments, the device comprises a seal arranged to close second end of the sample collection chamber, and wherein the sample collection conduit and/or the plunger is configured to break the seal when moved towards a second position in which the sample collection conduit is moved into the sample collection chamber.

In such a set of embodiments, the sample may be kept within the sample collection chamber until the sample collection conduit has been advanced into the sample collection chamber by a sufficient amount. When the sample collection conduit is advanced by a sufficient amount into the sample collection chamber, the sample collection conduit may conveniently be used to break, for example perforate, the seal at the second end of the chamber. Using the sample collection conduit to break the seal may further minimize the interaction of a user with the device, thus reducing the risk of contaminating the sample as well as the user. In embodiments wherein the sample collection conduit and plunger move together, the sample collection conduit may thus be advanced into the chamber to both break the seal and expel the sample from the sample collection chamber simultaneously. This may provide a simple and convenient means for operation of the sample collection device.

The seal may be any suitable seal which is capable of closing the second end of the sample collection chamber. For example, the seal may be a separate seal which is attached to the second end of the sample collection chamber during manufacture. However, in a set of embodiments, the seal is integrally formed with the sample collection chamber. For example, the seal may be formed integrally as part of the molding of the sample collection chamber, such that the sample collection chamber and seal together are one part. Integrally forming the seal with the sample collection chamber will reduce the number of components of the device, thereby potentially simplifying and reducing the cost of manufacture. The seal may be integrally provided in any suitable manner which allows it to be broken, e.g. perforated, or removed. In order to facilitate the breaking of the seal, the seal may have a wall thickness which is thinner than the wall thickness of the rest of the sample collection chamber such that the seal can easily be broken. In addition, or alternatively, the seal may comprise a number of weakened sections, which may comprise sections having a reduced wall thickness, which are designed to break upon the application of force, e.g. from the sample collection conduit.

As will be appreciated by those skilled in the art, oral fluid samples, such as saliva samples, typically comprise a volume of air within the sample. Often, the air is not beneficial when analyzing the sample, particularly as the air increases the perceived volume of the sample, but reduces the liquid content therein. Therefore, in a set of embodiments, the sample collection chamber comprises an air vent arranged to allow air to escape the sample collection chamber. Accordingly, as the sample passes through the sample collection conduit and collects in the sample collection chamber, air within the sample may separate from the liquid within the sample and the separated air may then escape the device through the air vent. The air may be allowed to separate from the liquid within the sample naturally. In addition or alternatively, the device may be agitated, e.g. by shaking, to encourage the separation of the air from the sample. Air which separates from the sample may freely escape via the air vent, which will leave a sample which has a higher percentage volume of liquid, thereby meaning that the volumetric marking, where provided, more closely represents the volume of liquid sample provided.

The air vent may comprise any suitable means which allows the venting of air from the sample collection chamber. For example, the sample collection chamber may comprise an opening on a sidewall of the sample collection chamber which allows air to escape.

The air vent may be positioned in any suitable manner which allows air to escape the sample collection chamber. The air vent may, at least with the plunger in a first position, be arranged below the plunger such that the plunger does not block the escape of air from the sample collection chamber. In a set of embodiments, the sample collection chamber comprises a maximum fill marking, wherein the air vent is arranged immediately above the maximum fill marking. As will be appreciated, in such embodiments, once the sample reaches the maximum fill level, any further sample added into the sample collection chamber via the sample collection conduit, will flow out of the sample collection device through the air vent. Accordingly, the air vent may also function to vent the sample when the sample collection chamber is overfilled. This may therefore ensure that the sample collection device is only capable of collecting and delivering the maximum volume of sample. This may help to ensure that any subsequent analysis of the sample is not impacted by a volume of sample which is too large for effective analysis.

In a set of embodiments, when the sample collection conduit is moved into an intermediate position in the sample collection chamber, the plunger is moved past the air vent such that the air vent is no longer in fluid communication with a space within the sample collection chamber in which the sample is contained. Accordingly, in the intermediate position the plunger acts to close at least the air vent, such that air or sample cannot escape the sample collection chamber. In embodiments as will be described in more detail below which comprise a seal at the second end, and wherein the sample collection conduit breaks the seal, the intermediate position may correspond to a position in which the sample collection conduit has not yet broken the seal. With suitable closing of the sample collection conduit, where necessary, this may therefore seal the sample collection chamber. The sample may then be stored, or even transported, within the sample collection chamber in a safe manner.

The sample collection conduit may be in direct fluid communication with the sample collection chamber such that the sample, or any other fluid, which passes through the sample collection conduit can pass directly into the sample collection chamber. However, in a set of embodiments, the device further comprises comprising a flow redirection chamber, arranged at the second end of the sample collection chamber, and wherein when in the first position the sample collection conduit extends into the flow redirection chamber, and wherein the sample collection conduit comprises a first conduit in fluid connection with the inlet of the sample collection conduit and the flow redirection chamber and a second conduit in fluid communication with the flow redirection chamber and the sample collection chamber, such that fluid can flow from the inlet through the first conduit, via the flow redirection chamber and into the sample collection chamber.

The presence of a flow redirection chamber, as well as first and second flow conduits, may provide a more turbulent flow path for the sample from the user to the sample collection chamber which may assist in the separation of air from the sample. Additionally, this arrangement of first and second conduits may, when the sample collection conduit is moved into a position in which the sample is expelled from the sample collection chamber, allow for simultaneous transfer of the sample out of the sample collection chamber, as well as venting of any chamber which the sample is transferred into. For example, if the sample collection chamber is connected to a further chamber, such as an analysis chamber, and with the sample collection conduit moved into a position in which the sample is expelled, the second conduit may provide a fluid connection with the further chamber, thereby allowing the transfer of the sample into the further chamber, and the first conduit may provide a vent from the further chamber to an outside of the device, e.g. to atmospheric pressure. As will be appreciated by those skilled in the art, this venting may minimize any pressure build-up within the further chamber and thus reduce the risk of any spraying of the sample, as the further chamber is filled, and also in the case where the further chamber is subsequently separated from the sample collection chamber. Venting in this manner may also make expelling of the sample into the further chamber easier as the pressure will be equalized.

In a set of embodiments, the sample collection conduit seals the flow redirection chamber at least in the first position such that fluid can only flow into the sample collection chamber via the second conduit. The flow redirection chamber may comprise an opening between the flow redirection chamber and the sample analysis chamber which the sample collection conduit passes through. The sample collection conduit may seal this opening such that the sample can only pass into the sample analysis chamber, from the flow redirection chamber, through the second conduit. Similarly, when the sample is expelled from the sample collection chamber, the sealing of the flow redirection chamber, for example the opening as mentioned above, may mean that the sample can only be expelled out of the sample collection chamber out through the second conduit.

The second conduit may comprise an outlet arranged to allow the sample to pass out of the second conduit into the sample collection chamber. In a set of embodiments, the second conduit comprises an outlet arranged to allow the sample to pass into the sample collection chamber, and wherein the outlet is arranged above a maximum fill marking of the sample collection chamber. Arranging the outlet in this manner may advantageously mean that as a user provides a sample, the sample flows through the sample collection conduit, through the first and second conduits, and falls out of the outlet, on the second conduit, down into the sample collection chamber. This may encourage the separation of air from the sample and may also ensure that the sample collected in the sample collection chamber cannot flow back into the sample collection conduit via the outlet, unless the sample collection device is tilted away from a vertical orientation. At the end of providing their sample, the user may blow into the sample collection conduit to force any remaining sample therein into the sample collection chamber. This arrangement with the outlet above the maximum fill level may thus mean that once the sample collection conduit is evacuated of any sample, the sample is unable to flow back into the conduit, at least when the sample collection conduit is in the first position and the device is held vertically. Therefore, if the sample collection conduit is used to break a seal, and as the sample is expelled out of the sample collection chamber through the second conduit, the first conduit will remain free of any sample and thus there will be minimal, or no, residual sample in the first conduit which can be forced out of the device by any air which vents therethrough. This may thus reduce the risk of the sample being ejected from the device.

In a set of embodiments, the device further comprises a restriction arrangement configured to prevent the sample collection conduit and/or the plunger from being retracted from the sample collection device as the sample collection conduit and/or the plunger is moved into the sample collection chamber. Such a restriction arrangement may advantageously ensure that a user cannot retract the sample collection conduit from the sample collection chamber, thereby preventing inadvertent contamination of the sample once it has been collected. The restriction arrangement may be achieved in any suitable manner. In a set of embodiments, the restriction arrangement may comprise a ratchet arrangement. For example, the sample collection conduit may comprise a set of teeth which engage with a pawl on the sample collection chamber. The pawl may be resiliently biased into contact with the teeth on the sample collection conduit. The pawl may be provided by any suitable means. In embodiments which comprise a seal arranged at second end of the sample collection chamber, the seal itself may provide the pawl when it is broken to allow the sample to be expelled out of the sample collection chamber. For example, the seal may split into at least one pawl, e.g. a plurality of pawls, when it is broken. The seal, and indeed the rest of the sample collection chamber, may be made from a material which is inherently resilient, e.g. plastic, such that the seal which forms the at least one pawl, the at least one pawl is inherently resiliently biased into the teeth on the sample collection conduit.

In a set of embodiments, the device further comprises a guide arrangement configured to prevent the sample collection conduit and/or plunger from rotating within the device for at least part of the range of linear movement of the sample collection conduit and/or plunger within the device. The guide arrangement may, for example, comprise a protrusion, e.g. a linear protrusion, extending along a length of the sample collection conduit and/or the plunger which is arranged to sit within a complementary shaped recess on the sample collection chamber, or a part connected thereto. Such a protrusion arranged within the recess may prevent the sample collection conduit from rotating. Preventing the sample collection conduit from rotating may be important in some embodiments. In embodiments in which the sample collection conduit comprises first and second conduits, with the second conduit comprising an outlet arranged above a maximum fill level and wherein an air vent is provided, it may be desirable to ensure that the outlet does not align with the air vent, as otherwise the sample may bypass the sample collection chamber and pass straight out of the air vent. Accordingly, through the use of a guide arrangement, it may be possible to ensure that the outlet and the air vent do not become aligned.

The guide arrangement may comprise a plurality of protrusions. The recess which receives the protrusion may provide the sole purpose of guiding the protrusions. However, in some examples, the recess may be provided by another part of the device and thus provide a dual function. For example, an air vent in the sample collection chamber may also function as a recess for the protrusion of the guide arrangement. The guide arrangement may be configured to only prevent rotation of the sample collection conduit and/or plunger for part of the range of linear movement of the sample collection conduit and/or plunger within the device. For example, it may only prevent rotation of the sample collection conduit and/or plunger for an initial portion of movement, e.g. from the first position to the intermediate position, and permit rotation when moving from the intermediate position to the second position.

The sample collection conduit may already be arranged in the first position when it is first used, e.g. when it is first taken out of its packaging if provided. In a set of embodiments, the device further comprises a first position fixing means for holding the sample collection conduit in the first position. By fixing the sample collection conduit in the first position, the sample collection device may be immediately ready for a user to deliver their sample. Additionally, by holding the sample collection conduit in the first position, a user may be prevented from accidentally pushing the sample collection conduit into the sample collection chamber before or during spitting into the sample collection conduit. In embodiments wherein the sample collection conduit and plunger are operatively linked, this can prevent movement of the plunger until the sample has been collected and is ready to be expelled. In another set of embodiments, the device may comprise the same or another position fixing means for holding the plunger in a first position, optionally as well as holding the sample collection conduit in the first position. In this first position the plunger may be held such that it is not moveable to expel the sample out of the sample collection chamber. Furthermore, in embodiments comprising a restriction arrangement as mentioned above, the position fixing means can prevent inadvertent movement of the sample collection conduit and/or plunger which may not be recoverable.

In another set of embodiments, the device further comprises an intermediate position fixing means for holding the sample collection conduit in an intermediate position, wherein in the intermediate position the plunger is positioned to close off an air vent in the sample collection chamber. Such an intermediate fixing means may advantageously hold the sample collection conduit, and the plunger, in an intermediate position at which the sample collection chamber is closed. This may allow the sample to be stored, at least temporarily, within the sample collection chamber.

In another set of embodiments, the device further comprises a second position fixing means for holding the sample collection conduit in a second position, in which the inlet of the sample collection conduit is contained within the sample collection device. Such a second position may also correspond to the plunger being advanced to expel all of the sample out of the sample collection chamber. Fixing the sample collection conduit in the second position may prevent the sample collection conduit from being retracted from the device once it has been fully inserted. This may reduce the risk of contamination of the sample, or indeed the risk of infecting others with the sample itself.

Any of the fixing means described above, for example the first position fixing means, intermediate position fixing means and/or the second position fixing means, may comprise any suitable arrangement which is capable of holding the sample collection conduit in its respective position. For example, the respective fixing means may comprise snap-fit arrangement arranged to snap onto and hold the sample collection conduit in position. In addition or alternatively, the fixing means may comprise an arrangement in which a protrusion engages within a corresponding recess. Such an arrangement may serve to hold the sample collection conduit in place until a sufficient force is applied to push the protrusion out of the recess. Any combination of fixing means may also be provided. For example, each of the first position, intermediate position, and second position fixing means may be different. Some or all of the fixing means may be overcome through the application of a sufficient force, i.e. a threshold force, such that the sample collection conduit may be moved. In order to hold the sample collection conduit in the respective positions, the first, intermediate or second position fixing means described above may engage with the sample collection conduit itself, or a part thereof, e.g. such as the plunger. For example, in embodiments wherein the movement of the sample collection conduit and plunger are operatively connected, fixing the position of the plunger may also fix the position of the sample collection conduit.

In certain instances, for example in embodiments in which the sample collection chamber comprises an air vent, if the user provides too much sample, the sample may overspill the sample collection chamber. Depending on the reason behind the sample collection, there is a risk that the sample may contain infected material, and thus overspill could cause the undesired infection of others or indeed cause contamination of other samples. Therefore, in a set of embodiments, the device further comprises an overspill chamber, arranged to collect any sample which overspills the sample collection chamber. The overspill chamber may therefore safely receive any sample which overspills the sample collection chamber. This may, for example, prevent an infected sample from passing onto a user's hands which may go on to touch other surfaces which others may come into contact with. The overspill chamber may take any suitable form. For example, it may comprise an annular chamber surrounding the sample collection chamber. The sample collection chamber and overspill chamber may together form a sample collection part.

In a set of embodiments, the device further comprises a conduit seal arranged outside and below the second end of the sample collection chamber, and wherein the sample collection conduit is configured to come into contact with the conduit seal so as to seal an outlet of the sample collection conduit, when the sample collection conduit is moved into a second position in which the sample collection conduit extends through the second end of the sample collection chamber. Accordingly, as will be appreciated by those skilled in the art, the sample collection conduit may be advanced into the second position so as to seal an outlet of the sample collection conduit. In this second position, the plunger may be fully advanced into the sample collection chamber such that the desired amount of sample has been expelled therefrom. In the case where a further chamber is attached to the sample collection chamber, sealing of the outlet of the sample collection conduit by the conduit seal may prevent any sample from being able to escape the further chamber back through the sample collection conduit. Sealing of the sample collection conduit may also prevent any further sample or fluid from being able to enter the further chamber.

The conduit seal may be achieved in any suitable manner. For example, the conduit seal may be provided on a further chamber which is connected to the sample collection chamber. Thus, when the sample collection conduit is advanced through the second end of the sample collection chamber into the further chamber, e.g. a sample analysis chamber, it may, as it reaches the end of its range of motion come into contact with the conduit seal. Alternatively, the conduit seal may be attached to the second end of the sample collection chamber.

In certain instances, it may be desirable to transport the sample either within the sample collection chamber, or within another chamber into which the sample has been transferred into. Therefore, in a set of embodiments, the device further comprises a cap arranged to close the sample collection chamber. The ability to close the sample collection chamber may allow the sample to be transported, e.g. to a testing facility, without the risk of the sample becoming contaminated, or indeed any risk of the sample leaking out of the device and potentially infecting others. In embodiments wherein a further chamber is attached to the sample collection chamber, the cap may function to seal both the sample collection chamber and the further chamber, e.g. a sample analysis chamber, as the further chamber may be sealed to the sample collection chamber.

As discussed above, with the sample expelled from the sample collection chamber, the sample collection conduit may be fully advanced into the sample collection chamber and extend out through the second end and may potentially be in fluid communication in a further chamber, e.g. an analysis chamber. In such instances, the sample collection conduit provides a fluid path between the analysis chamber and the outside of the device. When it is desired to store the sample within the analysis chamber, at least for a period of time, it may not be desirable to have this fluid path open for any extended prior of time. Therefore, in a set of embodiments the cap is arranged to seal the inlet of the sample collection conduit. Thus, as will be appreciated by those skilled in the art, in sealing the sample collection conduit, the cap may close, i.e. seal the sample collection chamber, as well as sealing the further chamber with which the sample collection conduit may be in fluid communication with.

The cap may be integrally provided with the sample collection device, e.g. it may be connected via a living hinge. This may advantageously mean that the cap is always provided with the device ready for closing the sample collection chamber and optionally the sample collection conduit. Additionally, in embodiments comprising an overspill chamber, the cap may also be arranged seal the overspill chamber. As with the embodiments described above, this may serve to prevent the leakage of potentially infected sample material.

Achieving a good, reliable, seal between the cap and the sample collection conduit may be particularly important to prevent the leaking or contamination of any sample from the device. Therefore, in a set of embodiments, a portion of the cap which seals the sample collection conduit is resiliently biased into a sealing position with the sample collection conduit. Through the biasing of the portion of the cap into a sealing position with the sample collection conduit, this may help to ensure that a high-quality seal is achieved between the cap and the sample collection conduit. Again, this may serve to help to ensure that no sample material is able to escape the sample collection device through the sample collection conduit. The resilient bias may help to ensure that a good seal is achieved irrespective of whether the sample collection conduit is fully inserted into the sample collection device.

It may be possible to reopen the cap once attached, e.g. to allow the sample to pass out of the device via the sample collection conduit. Alternatively, however, the cap may be configured such that once closed it cannot be reopened. This may be achieved in any suitable manner. For example, when in a closed position the cap may be flush with, or even below, a top surface of the sample collection device such that it is difficult, or even impossible, to reopen the cap. This may prevent the user from being able to interfere with the sample once it has been collected.

The sample may be expelled from the sample collection chamber into a number of different other components or devices. Thus, in a set of embodiments, the device further comprises a connection arrangement for connecting a further component to the device. The connection arrangement may be arranged at the second end of the sample collection chamber, or proximal thereto, such that the sample may be expelled out of the sample collection chamber into the further component. In at least some examples, the connection arrangement is positioned for a further component to be connected to the second end of the sample collection chamber. The further component could be, for example, a cap, a fluid transfer device (such as a syringe), a measurement chamber or a sample analysis chamber. The device may also additionally, or alternatively, comprise a connection arrangement for connecting a further component to the first end of the sample collection chamber.

The connection arrangement may comprise any suitable arrangement which may, for example, comprise a connection feature. For example, it may comprise a tapered portion for creating a friction fitting, a threaded fitting or a bayonet fitting. For example, the connection arrangement may comprise an internally, and/or externally, threaded collar. The further component may comprise a complementary connection feature which engages with the connection arrangement on the device. In the exemplary case where the connection arrangement comprises a threaded portion, the complementary connection feature on the further component may comprise a corresponding threaded portion. In embodiments in which the connection arrangement comprises a threaded portion, the threaded portion may be provided on a collar at the second end of the sample collection chamber, e.g. in a manner which surrounds the seal, where provided. The connection arrangement may, for example, conform to a connection standard such as the Luer, or Luer-lock connection standards. The connection arrangement may be configured to create a sealed connection with any further component that it is attached to.

The sample collection device may be used in any suitable manner in the collection and subsequent use of a sample. For example, the sample collection device may be used to collect, and temporarily store, a sample therein. In a set of embodiments, the sample collection device may further comprise a storage cap for attaching to the second end of the sample collection chamber. The storage cap may be in addition to the cap described above closes the sample collection chamber and optionally the sample collection conduit. The storage cap may be arranged to surround the seal at the second end of the sample collection chamber, where provided, such that the seal is protected from breaking until the storage cap is removed. This may therefore allow the device to be transported securely, e.g. to an analysis facility, without risk of the sample escaping the device. This may, for example, allow samples to be safely transported. The storage cap may thus ensure the safe storage of the sample within the device, specifically within the sample collection chamber. The storage cap may come pre-attached to the device, before it is filled, or it may be attached following the transfer of a sample into the device. The storage cap may comprise a complementary connection feature which engages with the connection arrangement described above, thereby facilitating the attachment of the storage cap to the sample collection chamber.

In situations in which the sample is temporarily stored within the sample collection chamber, e.g. when the sample is transported to a suitable analysis facility, the sample collection conduit and plunger may be partially advanced into the sample collection chamber into an intermediate position, as discussed above, such that any air vent within the sample collection chamber is closed such that the sample collection chamber is at least partially sealed. In a set of embodiments, the device further comprises a conduit cap configured to push the sample collection conduit into the sample collection chamber. The conduit cap may therefore be used to advance the sample collection conduit into the sample collection chamber, thereby removing the need for the user to directly contact the sample collection conduit, e.g. with their hand. As the sample collection conduit may have sample residue thereon, this may thus help to prevent the user from going on to contaminate other surfaces. The conduit cap may be used to push the sample collection conduit, and potentially the plunger, into the intermediate position such that the sample collection chamber is at least partially sealed, e.g. by closing off any air vent on the sample collection chamber through movement of the plunger.

The conduit cap may also be used to control the insertion of the sample collection conduit into the sample collection chamber, thereby potentially preventing the sample collection conduit from being inserted too far which may otherwise cause the penetration of the seal at the second end of the sample collection chamber. Additionally, the conduit cap may be used to seal at least part of the sample collection conduit. This may be by the conduit cap sealing around the sample collection conduit itself, e.g. at the inlet of the sample collection conduit, or by pushing the sample collection conduit into a sealing position with another sealing component, e.g. as described above with respect to the conduit seal. The conduit cap may also be configured to seal other parts of the device. For example, it may seal the sample collection chamber and/or the overspill chamber where provided In certain instances, it may be desirable to immediately transfer the sample into a container in which analysis of the sample may be performed. As mentioned above, the device may comprise a connection arrangement for connecting a further component to the device, for example to the second end of the sample collection chamber. The further component may therefore be a sample analysis chamber into which at least a portion of the sample can be expelled by the action of the plunger. Therefore, in a set of embodiments, the device further comprises a sample analysis chamber connected to the second end of the sample collection chamber. Analysis may then be performed on the sample within the sample analysis chamber itself, or the sample may be dispensed from within the sample analysis chamber onto a suitable device for analysis, e.g. an analysis machine.

Accordingly, as will be appreciated by those skilled in the art, the user may provide their sample directly into the sample collection chamber, using the sample collection conduit, and then at least a portion of the sample may be expelled by advancing the plunger into the sample collection chamber. Volumetric markings, where provided, on the sample collection chamber may be used to controllably expel a portion, or all, of the whole collected volume. This may thus allow a user to expel a desired volume of sample from the sample collection chamber. By transferring the sample directly into the analysis chamber, when the sample is taken for analysis there is less chance of contamination of the sample, or of contamination of other samples, as the sample does not need to be removed from the analysis chamber for analysis. Additionally, by providing the sample in the sample analysis chamber, the amount of processing at the analysis facility may be reduced. Given that in a typical analysis facility large numbers of samples are processed every day, removing even one pre-processing step may significantly reduce the burden on an analysis facility. The sample collection chamber and sample analysis chamber together form an assembly which may be fully assembled when provided to a user. Alternatively, the sample analysis chamber and sample collection chamber may be separate and the user may connect them together.

The analysis chamber may comprise a stabilization buffer configured to stabilize the sample within the sample analysis chamber. The stabilization buffer may comprise a Universal Transport Medium (UTM)®. The use of a stabilization buffer may help to ensure that the sample remains stable during transportation thus ensuring that analysis can be reliably performed on the sample. Of course, in addition or alternatively, the sample collection chamber could comprise a stabilization buffer such that the sample is stabilized in the sample collection chamber.

The sample analysis chamber may also comprise any other reagent which may be used in the analysis of a sample. Thus, in a set of embodiments, the sample collection device comprises a sample analysis chamber, configured to be connected to the second end of the sample collection chamber, for receiving the sample expelled from the sample collection chamber and wherein the sample analysis chamber comprises at least one reagent arranged therein.

Arranging a reagent within the sample analysis chamber may conveniently allow at least part of an analysis process, or a pre-analysis process, to be performed on the sample as soon as it is expelled into the sample analysis chamber. The reagent may thus interact with the sample as the sample is expelled into the sample analysis chamber. This may improve the process of providing and analyzing a sample, for a user. Additionally, it may further minimize the risk of contamination of the sample, which may otherwise occur if the sample analysis chamber has to be separated in order to add reagents thereto. The reagent may be any suitable reagent which may be used as part of the analysis of the sample. The reagent may be in a solid or fluid, e.g. liquid, form. The reagent may comprise material which mixes with the sample, and/or comprise material which interacts with the sample, e.g. as part of a chemical or biological process. The sample analysis chamber may be connected to the second end of the sample analysis chamber. This may minimize the chance of a user contaminating the sample analysis chamber. Alternatively, the sample analysis chamber may initially be separate from the sample collection chamber, and the user may selectively connect the sample analysis chamber to the second end of the sample collection chamber.

The reagent may be contained within the sample analysis chamber in any suitable manner. For example, the reagent may simply be present in a lower portion of the sample analysis chamber such that when the sample collects at the lower portion of the sample analysis chamber the sample mixes with the reagent. However, in a set of embodiments, the at least one reagent is contained within at least one capsule arranged within the sample analysis chamber. Providing the reagent within a capsule may simplify the addition of the reagent to the sample analysis chamber, e.g. during the manufacture of the device. For example, the capsule may simply be inserted into the sample analysis chamber during manufacture. As the reagent may remain stable within the capsule, manufacture of the device may thus not need to account for maintenance of the stability of the reagent. This may, therefore, simplify and improve manufacture. Containing the sample within the capsule may also preserve the reagent, which may otherwise degrade within the sample analysis chamber.

The sample analysis chamber may comprise a plurality of capsules, each capsule containing a reagent, e.g. a different reagent. The use of capsules may advantageously prevent any of the reagents contained therein from interacting with one another, until it is desired by the user. Additionally, by appropriately arranging the plurality of capsules within the sample analysis chamber, the order in which the sample comes into contact with the reagents contained within the capsules may be controlled. This may be particularly important when it is necessary that the sample is exposed to different reagents in a specific order to as to appropriately process the sample.

The at least one capsule may be supported within the sample collection chamber in any suitable manner. In a set of embodiments, the sample analysis chamber is shaped to support that at least one capsule within the sample analysis chamber. For example, the sample analysis chamber may have a circular cross section which tapers towards a bottom of the sample analysis chamber. The dimension of the cross-section, and a dimension of the capsule, e.g. the diameter thereof the capsule, may be chosen such that when the capsule is inserted into the sample analysis chamber, the capsule is supported by the internal walls of the sample analysis chamber.

In a set of embodiments, the sample analysis chamber comprises an internal rim arranged to support the capsule. The internal rim may provide a convenient means for reliably supporting the capsule within the sample analysis chamber at a specific position therein. Where multiple capsules are included, the sample analysis chamber may comprise multiple internal rims arranged along the length of the sample analysis chamber. Each of the internal rims may have different dimensions and thus be suitable for supporting different capsules. The internal rim(s) may be circumferential rim(s) which extend around the entire internal circumference of the sample analysis chamber.

The at least one capsule may be supported at any suitable position within the sample analysis chamber such that the sample can come into contact with the sample contained within the capsule. In a set of embodiments, the at least one capsule is supported in an upper portion of the sample analysis chamber. Arranging the at least one capsule in an upper portion of the sample analysis chamber may advantageously ensure that when the sample and the reagent contained within the capsule are mixed, there is space below the capsule for the mixture to fall, and thus be separate from the capsule.

Whilst in the embodiments described above, the analysis chamber may be shaped to support the at least one capsule, this is not essential. In another potentially overlapping set of embodiments the sample analysis chamber comprises a support structure on which the capsule is supported. In embodiments comprising a plurality of capsules, the sample analysis chamber may comprise a plurality of support structures. The use of a support structure may provide a convenient means for supporting the capsule within the sample analysis chamber which does not require the capsule to have a specific dimension or shape which makes it suitable to be supported by a shape of the sample analysis chamber. This may, therefore, allow a wider range of different capsules to be used with a given sample analysis chamber which may increase the number of potential applications of the device. The support structure may have any suitable form which is capable of supporting a capsule inside the sample analysis chamber. For example, the support structure may comprise a dish shaped structure, an outer rim of which engages with an internal wall of the sample analysis chamber to hold it in place. The support structure may act to seal the sample analysis chamber to form separate chambers therein. However, this is not essential, and the support structure may allow fluid communication therethrough.

In a further set of embodiments, the support structure is separable from the sample analysis chamber. Such a set of embodiments may advantageously mean that the support structure can be removed from the sample analysis chamber. This may be necessary for certain types of analysis which may be performed on the sample contained therein.

It may also be desirable to remove the capsule from the sample analysis chamber once the reagent therein has mixed with the sample. Thus, in a set of embodiments, the sample collection conduit is configured to engage the at least one capsule such that when the sample collection chamber is separated from the sample analysis chamber the at least one capsule is withdrawn from the sample analysis chamber by the sample collection conduit. As will be appreciated by those skilled in the art, such a set of embodiments provides a convenient means for separating the capsule from the sample analysis chamber without having to user other means which may cause contamination of the sample. In a similar manner, the sample collection conduit may also engage with a support structure where provided.

Any suitable means may be provided to achieve the above described engagement. In a set of embodiments, the sample collection conduit comprises a hook portion arranged to engage the at least one capsule. The hook portion may be defined by a protrusion or a recess on the sample collection conduit. In embodiments which comprise a restriction arrangement, the hook portion may also be provided by part of the restriction arrangement, e.g. a pawl arranged on the sample collection conduit. Such a hook portion may provide a reliable means for engaging the capsule which is suitable for withdrawing the capsule from the sample analysis chamber.

In order for the sample to mix with the reagent contained within the capsule, the capsule may have to first be broken, e.g. perforated, to allow the sample to come into contact with the reagent. In a set of embodiments, the sample collection conduit is configured to break the at least one capsule, and thereby allow the sample to interact with the reagent contained within the at least one capsule, when the sample collection conduit is moved from the first position towards a second position in which the sample collection conduit is advanced into the sample collection chamber. The sample collection conduit may break, e.g. perforate, the capsule thereby allowing mixing of the sample with the reagent contained therein. Use of the sample collection conduit may provide a convenient means for breaking the capsule, particularly as the sample collection conduit may be used to expel the sample from the sample collection chamber. This may, therefore, provide a device which is easy to use by a user, which may be particularly important if the device is being used by a user who provides the sample. Of course, the sample collection conduit need not necessarily break the capsule itself, and the sample collection conduit may force the capsule against another component which causes the capsule to break. For example, the sample collection conduit may force the capsule against a sharp edge, e.g. a pointed tip, within the sample analysis chamber.

The number of reagents contained within the sample analysis chamber may depend on the type of analysis which is going to be performed on the sample. In certain instances only a single reagent may be required, e.g. a stabilization buffer, so as to safely store the sample until further analysis is performed. However, in a set of embodiments, the at least one reagent comprises a plurality of reagents. The inclusion of a plurality of reagents within the sample analysis chamber may allow for more sophisticated processing of the sample within the sample analysis chamber, which may further minimize the risk of contamination which may otherwise occur if the sample analysis chamber is opened to introduce reagents. The at least one capsule may comprise a plurality of capsules each of which may contain a different reagent.

In another set of embodiments, at least two of the plurality of reagents are separated within the sample analysis chamber by a partition within the sample analysis chamber. The use of a partition may allow the reagents to be separated within the sample analysis chamber. In such embodiments, the reagents need not necessarily be contained within capsules, and instead the reagents may effectively be stored within sub-chambers within the sample analysis chamber, wherein the sub-chambers are defined by the partition. For example, first and second reagents may be separated by a partition extending therebetween. Of course, embodiments comprising a partition and those combining a capsule may be combined. For example, first and second reagents may be separated by a partition, and a third reagent may be provided in a capsule which is separated from the first and second reagents. Of course the number of partitions may depend on the number of reagents within the sample analysis chamber.

Depending on the form of the reagents, the partition may form sealed sub-chamber within the sample analysis chamber, and thus the partition may need to be broken in order to allow the sample, and the reagent it has mixed with, to progress through the sample analysis chamber towards another reagent. Thus in a set of embodiments, the sample collection conduit is configured to break the partition, and thereby provide a fluid connection between the plurality of reagents, when the sample collection conduit is moved from the first position towards a second position in which it is advanced into the sample collection chamber. The sample collection conduit may thus function in a similar manner described above with respect to the capsules. Again, this may provide a convenient means for breaking the partition, without requiring separate interaction by the user.

In a similar manner to that described above with respect to the capsule, it may also be necessary in some situations to remove the partition(s) from the sample analysis chamber.

Thus, in a set of embodiments, the sample collection conduit is configured to engage the partition such that when the sample collection chamber is separated from the sample analysis chamber, the partition is withdrawn from the sample analysis chamber by the sample collection conduit. Accordingly, the sample collection conduit may provide a convenient means for extracting the partition from within the sample analysis chamber. In a further set of embodiments, the sample collection conduit comprises a hook portion configured to engage the partition. The hook portion may provide the same advantages and comprise the same features as those discussed above.

It is discussed above how the sample collection conduit may be used to break the capsule and/or the partition. Depending on the form of the capsule or the partition, e.g. depending on the materials from which they are made, it may be possible for the sample collection conduit to break the capsule or the partition even if the sample collection conduit is blunt. However, this may require an increased force from the user in order to break the capsule or partition. Thus, in a set of embodiments, the sample collection conduit comprises a pointed tip which advances into the sample analysis chamber. The pointed tip may thus break the capsule and/or the partitions more easily, thus making use of the device easier for a user. The pointed tip may also at least partially define the hook portion where provided.

The type of the at least one reagent contained within the sample analysis chamber may depend on the type of analysis which is to be performed on the sample, and on the type of sample itself. In a set of examples, the at least one reagent comprises a lysis buffer. In embodiments wherein the sample is an oral fluid sample, the use of lysis buffer may advantageously be used to separate out RNA within the sample, which may be analyzed as part of analysis in determining whether a sample shows a subject has SARS-CoV-2.

In another set of embodiments, the at least one reagent comprises magnetic particles. The magnetic particles may be magnetic nano-particles. The magnetic particles may be capable of bonding with certain parts of the sample. For example, particularly in embodiments wherein the sample is an oral fluid sample and analysis is being performed on RNA, at least parts of the RNA may bind with the magnetic particles. Binding the RNA to the magnetic particles may provide a convenient means for separating the RNA from the rest of the sample, e.g. through the use of a magnetic field, which may be required in order to perform analysis on the RNA.

In another set of embodiments, the at least one reagent comprises a stabilization buffer. The use of a stabilization buffer may advantageously provide a means for ensuring the stability of the sample within the sample analysis chamber, which may be particularly important if there is a chance the sample may be stored in the sample analysis chamber for a period of time before analysis is performed.

As discussed above, the reagent may comprise magnetic particles, e.g. magnetic nano-particles, which may bind with parts of the sample. In order to separate the parts of the sample which bind to the magnetic nano-particles, from the rest of the sample, it may be necessary to apply a magnetic field to the sample so as to attract the magnetic particles, and subsequently drain away the rest of the sample. Thus, in a set of embodiments, the device further comprises a magnetic device configured to apply a magnetic field to the sample analysis chamber. The magnetic field may be used to separate magnetic components from non-magnetic components within the sample, and any reagent mixed therewith.

The magnetic device may be in engagement with the sample analysis chamber, so as to apply a magnetic field to the sample analysis chamber. The magnetic device may engage a substantial portion of the sample analysis chamber. The magnetic device may wrap around the sample analysis chamber. The magnetic device may be capable of being attached to the sample analysis chamber. The magnet device may be attached to the sample analysis chamber by any suitable means. For example, a friction fitting may be utilized to secure the magnet to the sample analysis chamber. The magnetic device may be selectively engaged with the sample analysis chamber, e.g. by being held against the sample analysis chamber, as required.

The magnetic device may comprise a permanent magnet which creates a permanent magnetic field. In another set of embodiments, the magnetic device may comprise an electromagnetic device which is capable of selectively generating a magnetic field. The use of an electromagnetic device may advantageously allow for the magnetic field to be turned on and off, thereby allowing manipulation of the sample without having to necessarily separate the magnetic device from the sample analysis chamber. In a further set of embodiments, the magnetic device is configured to be engaged with, e.g. attached to, an outside of the sample analysis chamber. Engaging the magnetic device with an outside of the sample analysis chamber may reduce any risk of the magnet causing contamination of the sample, e.g. due to a substance presence on the magnet.

The magnetic device may be re-used with multiple sample analysis chambers. The magnetic device may form part of a further apparatus, e.g. a sample analysis apparatus. Such an apparatus may perform processing and optionally analysis of the sample contained within the sample analysis chamber.

In another set of embodiments, the magnetic device is engaged with a lower portion of the sample analysis chamber. Attaching the magnet to the bottom of the sample analysis chamber may provide a convenient means for holding any magnetic material within the sample analysis chamber, whilst allowing other material to be dispensed from the sample analysis chamber.

Following mixing of the sample with the at least one reagent within the sample analysis chamber, it may no longer be necessary for the sample collection chamber to be connected to the sample collection chamber. Thus, in a set of embodiments, the sample analysis chamber is separable from the sample collection chamber. As described above, this may be facilitated by a connection arrangement provided on the sample collection chamber which interacts with a corresponding connection arrangement provided on the sample analysis chamber. For example, they may be engaged via a threaded engagement, a push-fitting, or any other suitable fixing means which secures the sample collection chamber and sample analysis chamber together. Thus, the sample analysis chamber may conveniently be separated from the sample collection chamber. This may, for example, allow for further analysis to be performed on the sample which is combined with the at least one reagent within the sample analysis chamber. Additionally, the sample and the at least one reagent which has been mixed or interacted with the sample may be dispensed from the sample analysis chamber into another device, e.g. an analysis machine.

When separated from the sample collection chamber, it may be desirable to close the sample analysis chamber as the sample contained therein may be stored for a period of time.

Thus, in a set of embodiments, the sample analysis chamber further comprises a cap for closing the sample analysis chamber.

Although the sample analysis chamber has been described above in combination with the sample connection chamber, the sample analysis chamber comprising at least one reagent arranged therein may be considered novel and inventive in its own right and thus when viewed from a further aspect the present invention provides a sample analysis chamber comprising at least one reagent arranged therein. The sample analysis chamber of this further aspect of the invention may comprise any of the features described above with respect to the sample analysis chamber and advantages of such features equally apply.

Whilst the presence of a reagent within the sample analysis chamber has been described above, any other component which may be used as part of the analysis process may be contained within the sample analysis chamber such that it is present therein when the user provides their sample and expels the sample from the sample collection chamber. For example, the sample analysis chamber may comprise an absorbent body which absorbs a portion of the sample within the sample analysis chamber. Of course the sample may have mixed with at least one reagent by the point at which it is absorbed by the absorbent body. The absorbent body may, for example, be in the form of a sponge. The absorbent body may be configured, e.g. through appropriate dimensions, to absorb a certain volume of sample. The absorbent body may be removed from the sample analysis chamber and placed onto an analysis machine. The use of such an absorbent body may provide a convenient means for extracting a set volume of sample from the sample analysis chamber.

Further features relating to the sample collection device will now be described. The sample collection conduit may be dimensioned such that when the sample analysis chamber is connected to the sample collection chamber, and when the sample collection conduit is fully inserted into the sample collection chamber, the sample collection conduit does not contact the sample dispensed into the sample analysis chamber, at least when the device is held in a vertical position with the sample analysis chamber arranged below the sample collection chamber. Such an arrangement will allow the sample to freely flow from the sample collection chamber into the sample analysis chamber and reduce the chance of any sample flowing back through the sample collection conduit.

The sample analysis chamber may also comprise a complementary connection feature, such as an external thread, for engaging with the connection arrangement on the sample collection chamber where provided. The sample analysis chamber may be separable from the sample collection chamber. By facilitating separation, the sample collection chamber may be separated from the storage chamber in order to perform analysis on the sample.

In another set of embodiments, a dispensing chamber may be attached to the sample collection device. The dispensing chamber may comprise a dispense outlet which the sample may be dispensed from. The dispense outlet may initially be closed by a seal which may be removed in order to dispense the sample out through the dispense outlet. The dispense outlet, and the dispensing chamber, may be configured such that the sample can be dispensed from the outlet on a drop-by-drop basis. For example, the dispense chamber may be made from a deformable material, e.g. plastic, which a user may squeeze in order to dispense the sample out through the dispense outlet. The dispense outlet may be dimensioned to restrict the flow of the sample therethrough. This may allow a user to accurately dispense a small amount of the sample, e.g. onto a testing tray which may be inserted into an analysis machine. The dispense chamber may be manufactured by any suitable means. For example, the dispense chamber may be manufactured using a blow-fill-seal technique or by injection molding a material such plastic, as rubber, or any other suitable material.

As discussed above, the sample collection conduit and plunger may be integrally provided with one another, and thus a user may push the sample collection conduit in order to move the plunger within the sample collection chamber and expel the sample therefrom. However, depending on the volume of the sample within the sample collection chamber, and the volume of air in the chamber, e.g. the sample analysis chamber, into which the sample is expelled, it may be desirable to allow air to vent out of the sample collection conduit to outside of the sample collection device, e.g. to atmospheric pressure. This air may simply pass out through the inlet of the sample collection conduit if the user's hand does not fully close the inlet. However, in a set of embodiments, the sample collection conduit comprises an air vent arranged to allow air to escape to an outside of the sample collection device. The air vent may be arranged proximal to an inlet end of the sample collection conduit such that when a user provides a sample, their mouth seals around the air vent, thus preventing the escape of any sample out of the sample collection conduit.

The sample collection conduit may comprise a mouthpiece configured to allow a user to seal their mouth around the sample collection conduit when providing an oral sample. Such a mouthpiece may allow a user to achieve a better seal around the sample collection conduit when providing a sample and thus the chance of leaking of the sample may be reduced. As the sample may comprise infected material, reducing the risk of any leakage, which could potentially infect others, is particularly advantageous.

The sample collection conduit may comprise a tapered friction fitting at its inlet. The tapered fitting may, for example, conform to the Luer standard. This may advantageously allow a sample to be inserted into the sample collection device, through the sample collection conduit, if the sample is contained within other means having a fitting capable of connecting with the tapered friction fitting. The sample collection conduit may comprise other connection means, e.g. such as a threaded portion. Such a threaded portion may conform to the Luer-lock standard.

The sample collection device may further comprise an adaptor configured to be attached to the second end of the sample collection chamber. The adaptor may allow the sample collection device to be used to transfer the sample to any one of a number of different components or devices. This may advantageously increase the number applications the sample collection device can be used with.

The sample collection device may be made from any suitable material or combination of materials. As mentioned above, part or all of the sample collection device may be at least partially transparent, e.g. fully transparent, such that the user can see their sample as it passes into the device. The sample collection chamber may be made from polypropylene and the plunger may be made from polyethylene or polycarbonate. At least in those embodiments wherein the plunger and conduit are integrally formed, the conduit may also be made from polyethylene or polycarbonate. Such an embodiments may advantageously remove the need to provide an O-ring between the plunger and the sample collection chamber, as well as removing the need to provide a lubricant to lubricate the movement of the plunger. Removing such lubricant may be advantageous as the lubricant may potentially affect the results of any testing performed on the sample.

Whilst the various parts of the device have been described as being attached together above, the device may be provided with each of the component separately, e.g. as a kit of parts. For example, the kit of parts may comprise the sample collection chamber with the sample collection conduit and plunger inserted therein, provided with a separate sample analysis chamber which may be selectively attached by the user as desired. Any combination of different components as described above may be provided in the kit of parts.

As will be appreciated by those skilled in the art, whilst the device may be particularly well suited to the collection of an oral fluid sample, as described in some of the embodiments above, the device may also be used for the collection, measurement and transfer of other fluid samples, other than oral fluid samples. For example, fluid samples may be transferred directly into the device, e.g. from another device such as a syringe.

BRIEF DESCRIPTION OF THE DRAWINGS

Some preferred embodiments of the present invention will now be described, by way of example only, and with reference to the following drawings, in which:

FIGS. 4A and 4B show different perspective views of the sample collection conduit and plunger shown in FIG. 1;

FIGS. 12A-12C show three different view of a secondary cap;

FIG. 13A-13B show two different view of a transport cap;

FIGS. 16A-16B show two different perspective views of a sample analysis chamber in accordance with another embodiment of the present invention;

FIGS. 25A-25E show cross-sectional views of a sample collection device in accordance with another embodiment of the present invention which comprises first and second reagents within the sample analysis chamber;

FIGS. 26A-26J show cross-sectional views of a sample collection device in accordance with another embodiment of the present invention which comprises first and second reagents within the sample analysis chamber.

DETAILED DESCRIPTION

Figure 1:
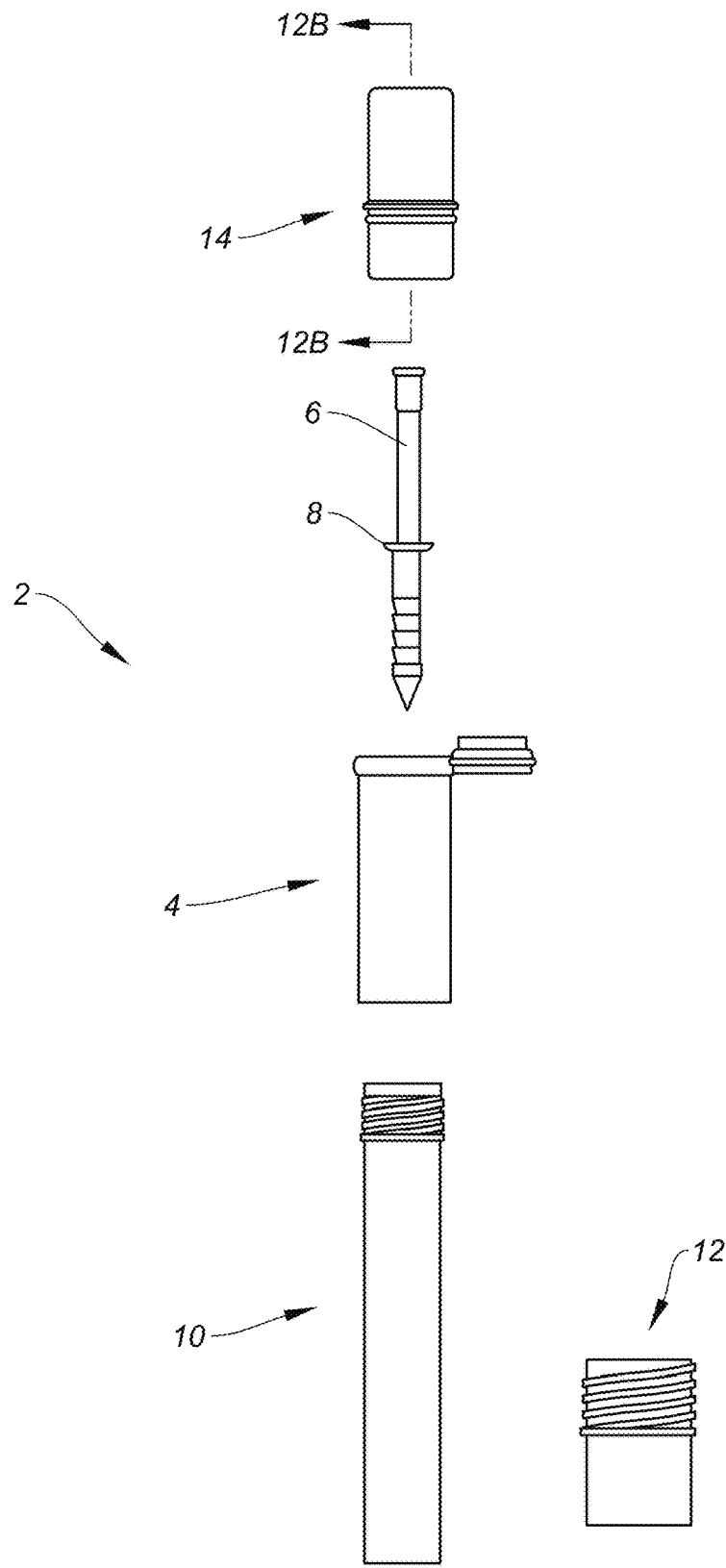
FIG. 1 shows an exploded side view of a sample collection device in accordance with an embodiment of the present invention.

FIG. 1 shows an exploded view of a sample collection device 2, hereinafter the "device" 2, in accordance with an embodiment of the present invention. The device 2 comprises a sample collection part 4 which comprises a sample collection chamber and overspill chamber as will be described in more detail with reference to later Figures. The device 2 further comprises a sample collection conduit 6 with an integrally formed plunger 8. A sample analysis chamber 10 is provided which may be attached to the sample collection part 4. Also provided is a storage cap 12 which may be secured to the sample collection part 4 instead of the sample analysis chamber 10. Further, a conduit cap 14 for use in partially advancing the plunger 8 into the sample collection part 4 is included. These components will all be described in detail with reference to later Figures.

Figure 2:
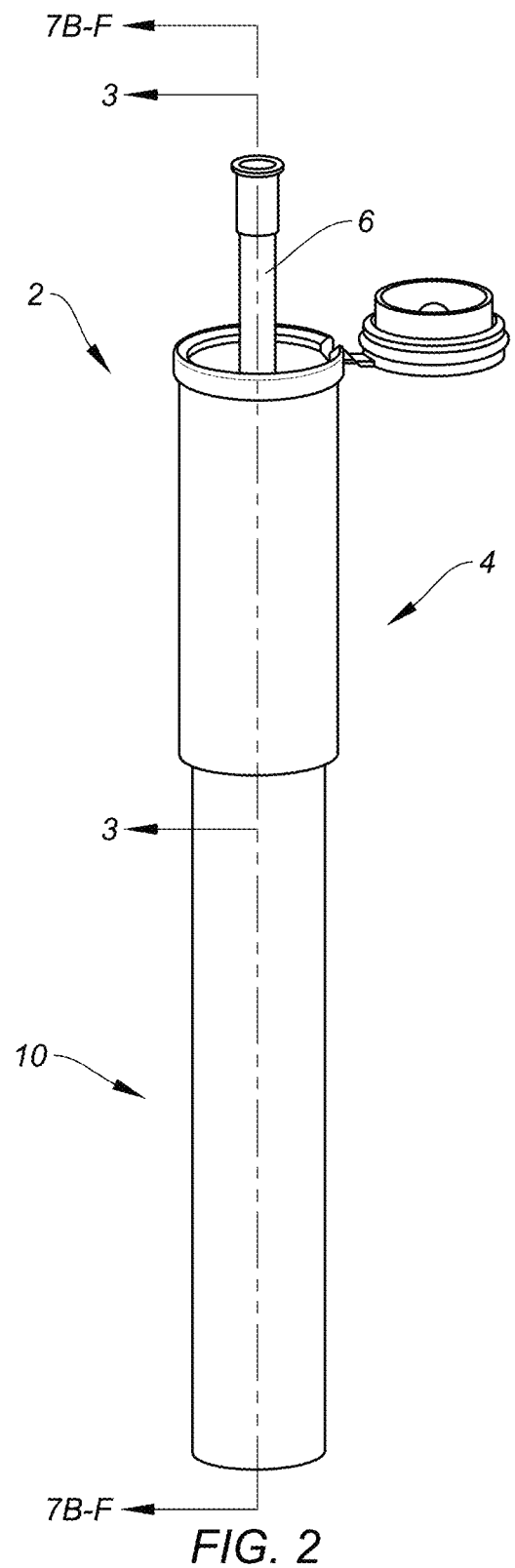
FIG. 2 shows a perspective view of the sample collection device shown in FIG. 1 with some of the components assembled together.

FIG. 2 shows a perspective view of the sample collection device 2 shown in FIG. 1 in an assembled form. In the view shown, the sample collection part 4 is connected to the sample analysis chamber 10, and the sample collection conduit 6 is inserted within the sample collection part 4 in a first position. The sample collection device 2 may be provided in the arrangement shown in FIG. 2 for a user ready for the user to provide a sample.

Features of the sample collection part 4 are described in more detail with reference to FIG. 3 which shows a side cross sectional view through the sample collection part 4 with the sample collection conduit 6 and plunger 8 inserted therein in a first position. The sample collection conduit 6 and plunger 8 are formed together integrally as a single component. Accordingly, their movement is operatively coupled such that movement of the sample collection conduit 6 results in movement of the plunger 8. The sample collection part 4 comprises a sample collection chamber 16 which is at least partially defined by an inner cylindrical wall 18. The inner cylindrical wall 18 comprises a first position fixing means 20, an intermediate position fixing means 22, and a second position fixing means 24. Each of the fixing means 20, 22, 24 comprises an annular protrusion extending into the sample collection chamber 16. Each of the fixing means 20, 22, 24 is dimensioned and shaped such that the plunger 8 is able to pass the fixing means 20, 22, 24, only when sufficient force is applied.

As will be appreciated by those skilled in the art, the first position fixing means 20, may hold the sample collection conduit 6 in the first position shown. The intermediate position fixing means 22, together with the first position fixing means 20, may hold the sample collection conduit in an intermediate position, in which the plunger is arranged between the intermediate position fixing means 22 and the first position fixing means 20. The second position fixing means 24, together with the base 25 of the sample collection chamber 16. Accordingly, the fixing means 20, 22, 24 act to hold the plunger 8, and hence the sample collection conduit in the respective positions. Whilst the first, intermediate and second fixing means 20, 22 and 24 are shown as annular protrusions, any other form of fixing means may be provided which is capable of holding the sample collection conduit 6 in the respective positions.

Figure 3:
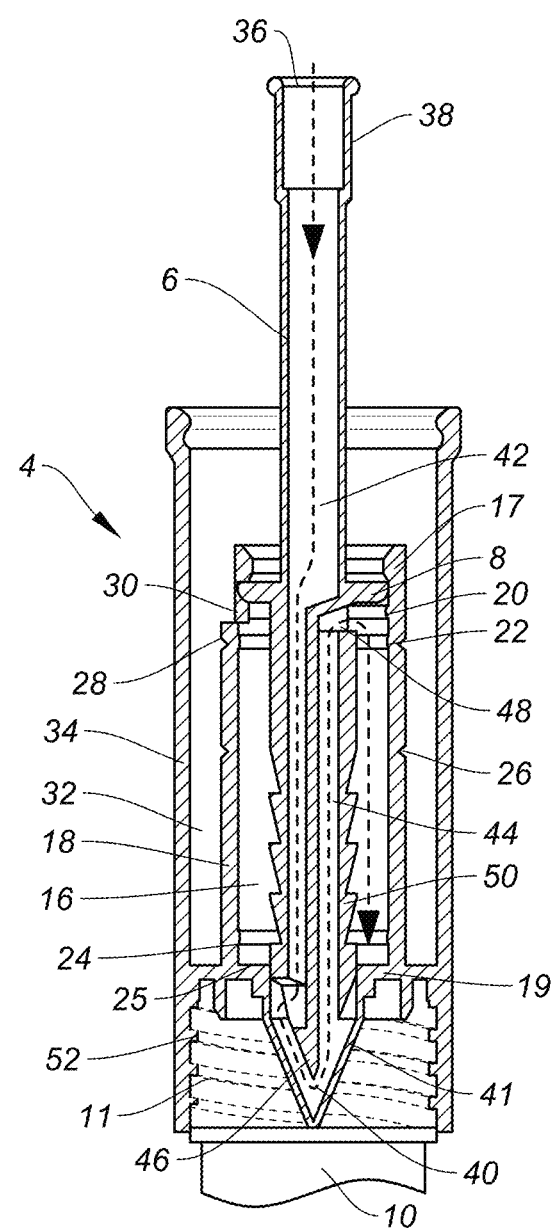
FIG. 3 shows a side sectional view of the sample collection device of FIG. 1 focusing on the sample collection chamber.

As shown in FIG. 3, the sample collection chamber 16 and plunger 8 are dimensioned such that the plunger 8 fits tightly within the sample collection chamber 16. The sample collection chamber may be made from polypropylene and at least the plunger may be made from polyethylene such that there is no need to include a separate sealing O-ring or any need to lubricate the sample collection chamber 16. This may thus reduce the number of components required for the device 2. Of course, any other suitable materials may be selected to achieve the same effect.

The sample collection chamber 16 further comprises a minimum volumetric marking 26 and a maximum volumetric marking 28 which may be used as a guide when a user is filling the sample collection chamber. The minimum volumetric marking may correspond to 1 ml and the maximum volumetric marking may correspond to 1.5 ml. Such sample markings may be well suited for the collection of a sample for use in COVID-19 analysis. Of course, the volumetric markings may be set specifically depending on the purpose of the sample collection. Arranged immediately above the maximum volumetric marking is an air vent 30 which may function to allow air to escape the sample collection chamber 16 as it is filled with a sample. The air vent 30 may allow air to vent to an outside of the device 2, e.g. via the overspill chamber 32 in the embodiment shown, or into another chamber of the device 2. Of course, the air vent 30 may be arranged at any suitable position to allow the venting of air and it need not necessarily be arranged immediately above the maximum fill marking 28. The air vent 30 may also allow liquid sample to pass therethrough as will be described below with reference to later Figures. As shown in the Figure, with the sample collection conduit 6 in the first position, the plunger 8 does not close the air vent 30 and thus air is free to escape. The device 2 further comprises an overspill chamber 32 arranged to receive any sample which overspills the sample collection chamber 16, particularly any sample which passes out through the air vent 30. The overspill chamber 32 has an annular shape around the around the sample collection chamber 16 and is defined by a cylindrical outer wall 34 of the sample collection part 4.

In the embodiment shown, the sample collection conduit 6 and plunger 8 are integrally formed. For example, they may be formed as part of a single molding process. Of course, the sample collection conduit 6 and plunger 8 could be provided by separate components. In the position shown in FIG. 3, the sample collection conduit 6 is in the first position in which the sample collection conduit 6 extends from within the sample collection chamber 16 to an outside of the device 2, out through the first end 17 of the sample collection chamber 16, such that the inlet 36 is outside the sample collection chamber 16 and outside the device 2. The sample collection conduit 6 comprises a mouthpiece 38, at the inlet 36, which a user may engage when providing a sample.

The sample collection conduit 6 extends through the sample collection chamber 16 to a flow redirection chamber 40 which is arranged at the bottom of the sample collection chamber 16. The flow redirection chamber comprises an opening which is closed and sealed by the seal 41. The flow redirection chamber 40 and seal 41 therefore define the second end of the sample collection chamber 16.

The sample collection conduit 6 comprises a first conduit 42 which extends from the inlet 36 into the flow redirection chamber 40, and a second conduit 44 which extends from the flow redirection conduit to the sample collection chamber 16. The sample collection conduit 6 comprises a pointed end 46, which may for example have a conical profile, for breaking the seal 41 when the sample collection conduit 6 is moved towards a second position.

The second conduit 44 comprises an outlet 48 which is arranged such that in at least the first position the outlet 48 is above the maximum fill marking 28 on the sample collection chamber 16. The dashed arrow on the Figure shows the flow of sample during the transfer of a sample into the sample collection chamber. The sample may flow from the inlet 36, through the first conduit 42, into the flow redirection chamber, up through the second conduit 44, and out through the outlet 48 into the sample collection chamber 16. As shown, the outlet 48 is arranged on the opposite side within the sample collection chamber to the air vent 30. This prevents the sample from passing out through the outlet 48 and directly out the air vent 30 into the overspill chamber 32.

The sample collection conduit comprises a plurality of teeth 50 extending along part of its length. These teeth 50 together with the seal 41 when broken form a ratchet arrangement for preventing retraction of the sample collection conduit 6 once it has been inserted into the sample collection chamber 16 by a sufficient amount. This will be described in more detail below with reference to later Figures. However, as will be appreciated by those skilled in the art, the ratchet arrangement may only come into effect once the sample collection conduit 6 has been inserted by a sufficient amount.

Arranged at the second end 19 of the sample collection chamber 16 is an internally threaded collar 52. The internally threaded collar 52 may be used to attach the sample collection part 4, specifically the sample collection chamber 16 thereof, to another component. The internally threaded collar 52 may thus form a connection arrangement. In the embodiment shown, an external thread 11 on the sample analysis chamber 10 is connected to the internally threaded collar 52. Whilst an internally threaded collar 52 is illustrated, the device 2 may comprise any other suitable connection arrangement.

Figure 6:
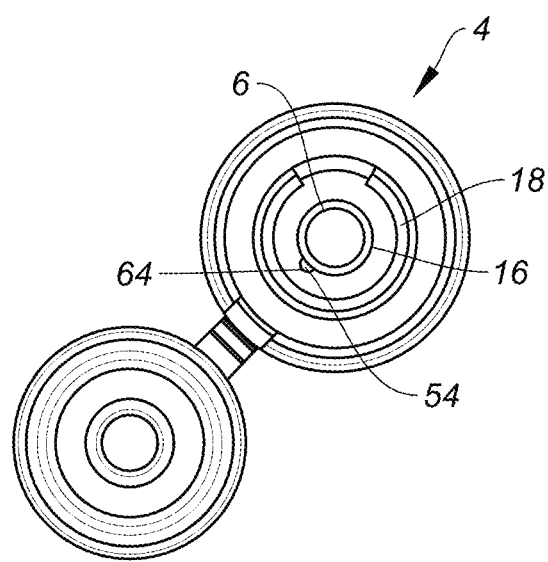
FIG. 6 shows an end-on view of the sample collection chamber shown in FIG. 5.

FIG. 4A shows the sample collection conduit 6 and plunger 8 in isolation and in an isometric view. In this Figure, the outlet 48 and conical pointed end 46 can be seen more clearly. Additionally, the shape of the teeth 50 can also be seen more clearly. The sample collection conduit 6 further comprises a linear protrusion 54 which extends along part of the length of the sample collection conduit 6. The linear protrusion 54 engages with a corresponding recess, as shown in FIG. 6. Together, the linear protrusion 54 and the recess form a guiding arrangement which prevents the sample collection conduit 6 from rotating. In FIG. 4A an inlet 56 to the second conduit 44 is also visible. FIG. 4B shows the sample collection conduit 6 and plunger 8 in a different isometric view and shows an outlet 58 of the first conduit 42 (not visible in this Figure).

Figure 5:
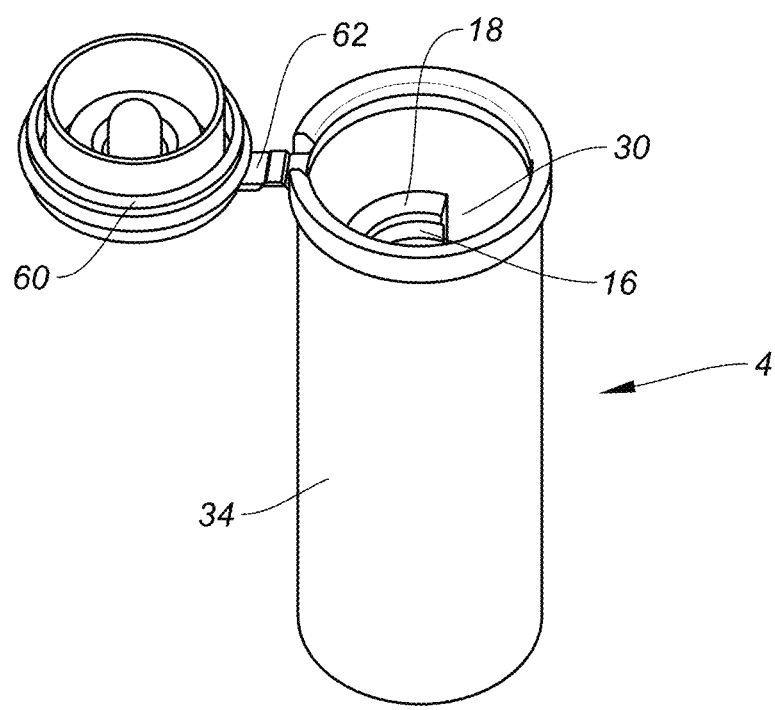
FIG. 5 shows a perspective view of the sample collection chamber shown in FIG. 1.

FIG. 5 shows an isometric view of the sample collection part 4 in isolation, without the sample collection conduit 6 therein. In this view, the top of the outer wall 18 of the sample collection chamber 16 is just visible, and the air vent 30, which is formed by a cutaway in the outer wall 18, is also visible. The sample collection part 4 comprises a cap 60 which is connected via a living hinge 62 to the outer wall 34 of the sample collection part 4. The cap 60 and the rest of the sample collection part 4 may be formed integrally as a single component, thus reducing the number of separately manufactured components.

FIG. 6 shows an end-on view of the sample collection part 4, when viewed looking through down through the first end 17 of the sample collection chamber 16. A recess 64 is provided which receives the linear protrusion 54 of the sample collection conduit 6, and therefore prevents rotation of the sample collection conduit 6 within the sample collection chamber 16.

FIG. 7A-7F demonstrate use of the sample collection device 2. In the embodiment illustrated, the sample analysis chamber 10 is connected to the sample collection part 4. Of course, it may be the case that no other component is connected to the sample collection part 4, or another suitable component may be attached. As shown in FIG. 1, in order to provide a sample, a user 66 first places their mouth 67 around the mouthpiece 38 (no longer visible) of the sample collection conduit 6. They are then able to deposit their oral fluid sample via the inlet 36 (also not visible in this Figure).

Figure 7A:
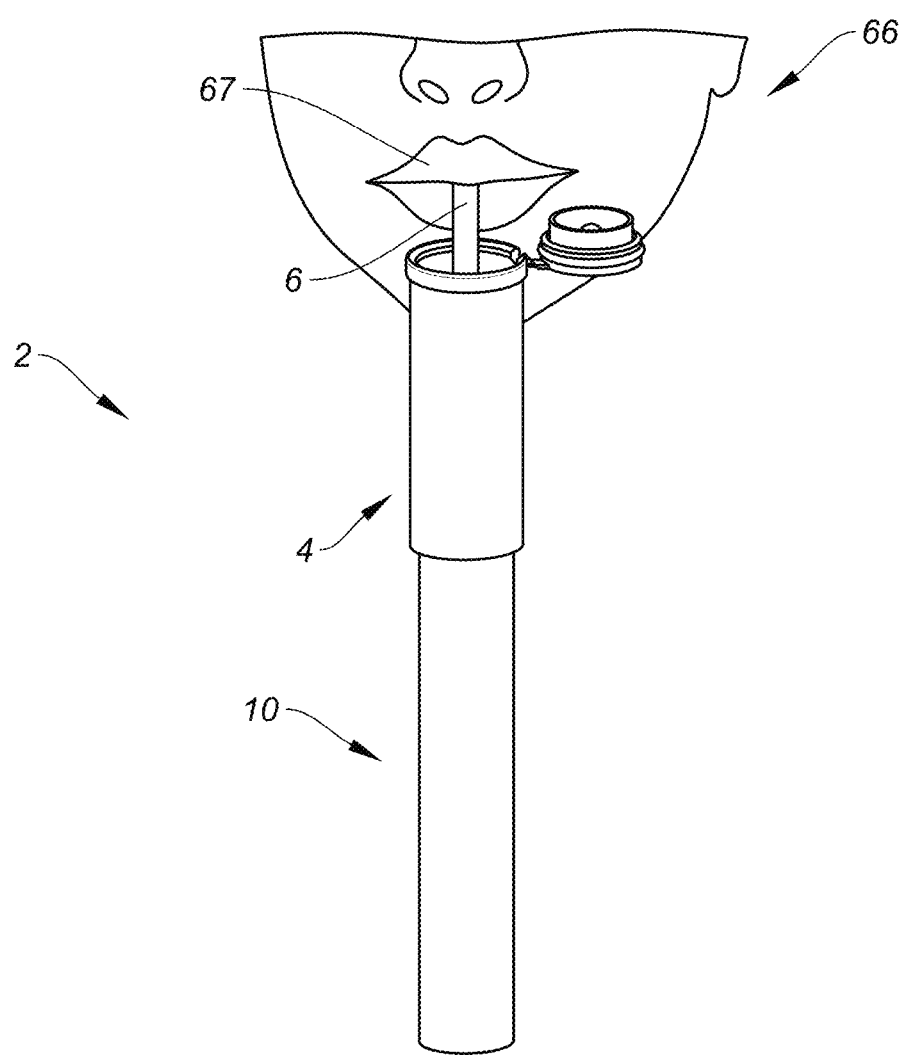
FIGS. 7A-7F illustrate the transfer of a sample into the sample collection device shown in FIG. 1.
Figures 7B, 7C, 7D:
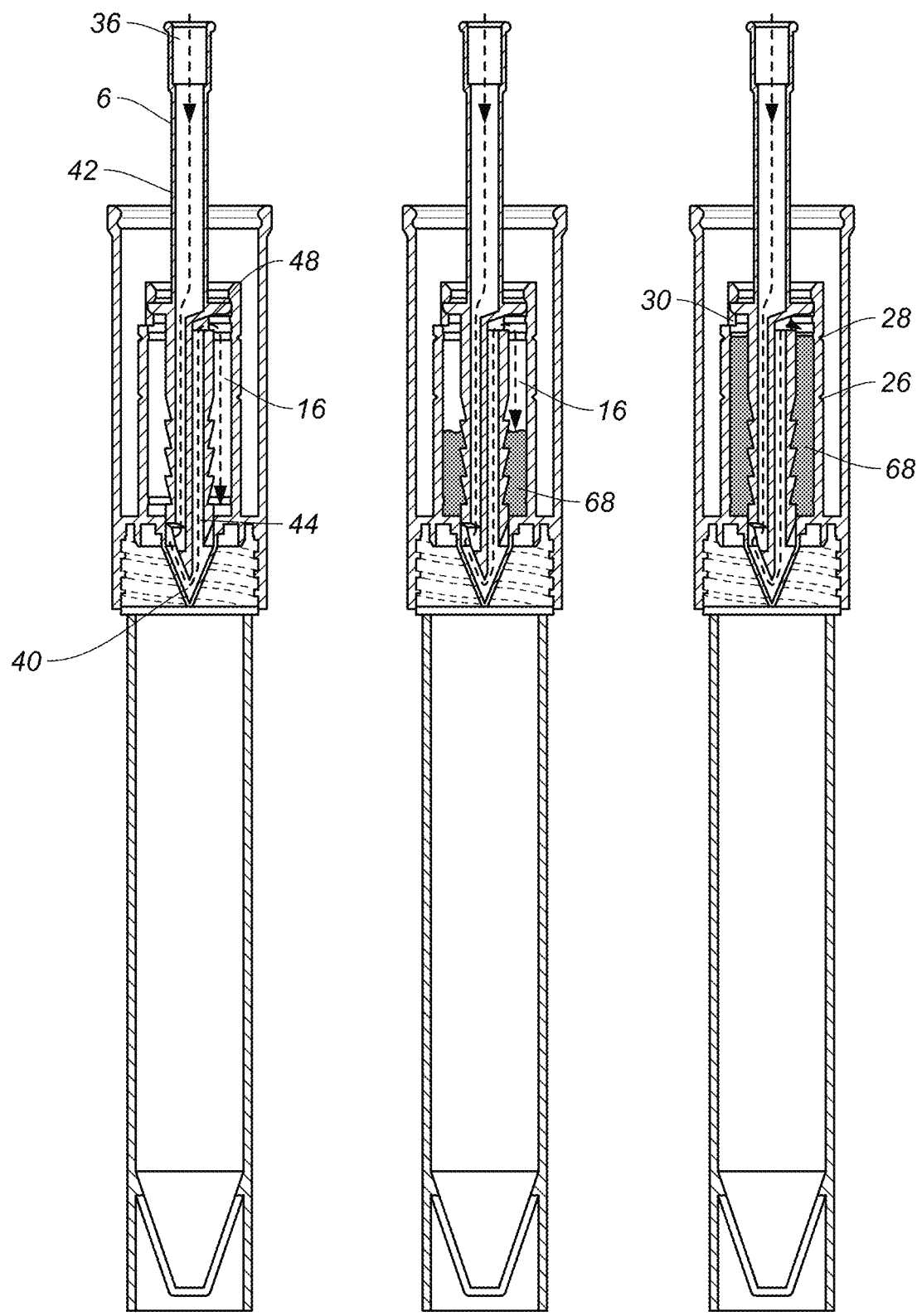

FIG. 7B-7F show the filling of the sample collection chamber 16 with the sample. In these Figures, the dashed line with the arrows along its length represents the flow of the sample within the device 2. As shown in FIG. 7B, the sample flows from the inlet 36 through the first conduit 6, of the sample collection conduit 6, through the flow redirection chamber 40, up through the second conduit 44 and out through the outlet 48 where it is free to fall into the sample collection chamber 16.

As the user provides their sample, the sample 68 begins to collect in the sample collection chamber 16, as shown in FIG. 7C. A user may continue to provide their sample via the sample collection conduit 6, until the sample reaches the maximum fill marking 28 as shown in FIG. 7D. Of course, they may instead only provide their sample until it reaches the minimum fill marking 26 or anywhere therebetween. Once the sample 68 is between the minimum and maximum fill markings 26, 28, the user may stop providing their sample 68. During this process, any air within the sample collection chamber 16 is free to escape via the air vent 30.

Figures 7E, 7F:
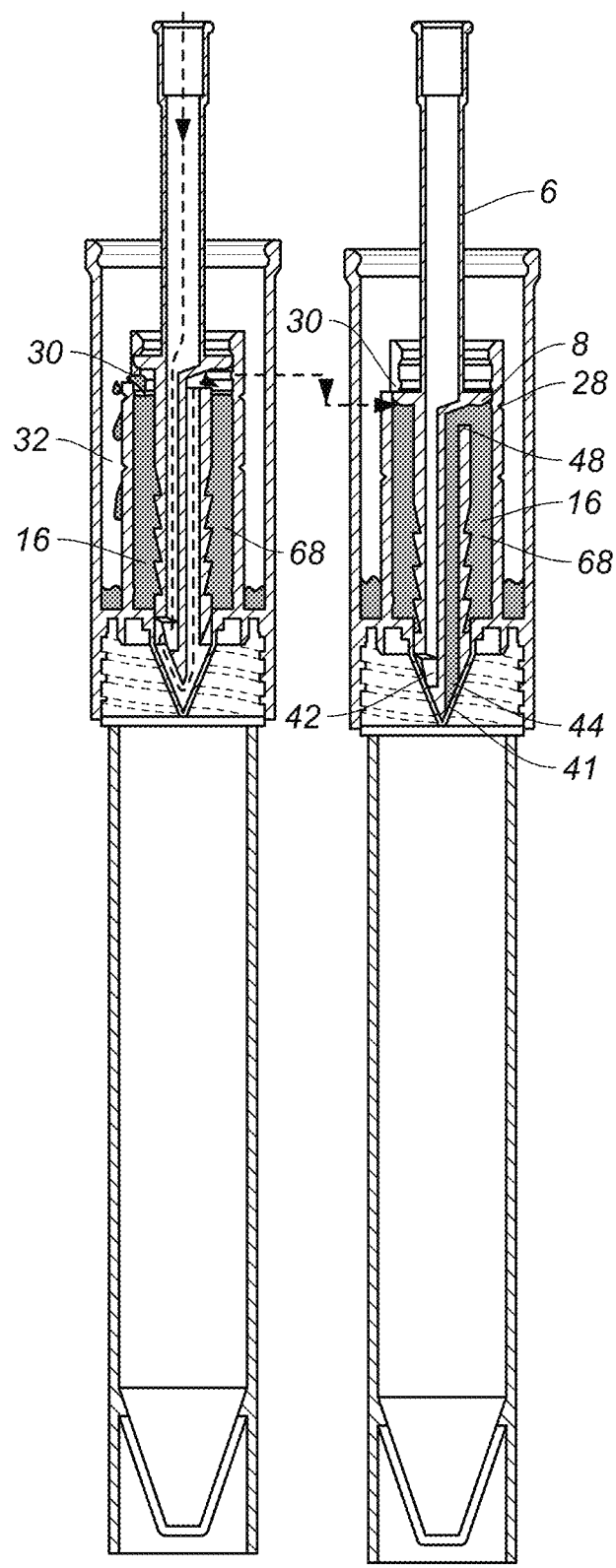

Once the user has filled the sample collection chamber 16 to the desired level, the user may then evacuate the sample collection conduit 6 of any remaining sample therein. This may be achieved by the user blowing through the sample collection conduit 6. This is shown in FIG. 7E. The blowing of the remaining sample may cause the sample 68 to overspill the sample collection chamber 16, out through the air vent 30 and collect in the overspill chamber 32. The overspill chamber 32 therefore advantageously collects any overspill, thus reducing the risk of the sample 68 going on to contaminate other surfaces. The overspill chamber 32 may also collect any overspill during the filling of the sample collection chamber 16 with the sample 68, even before the user blows through the sample collection conduit 6, in the event that the user provides too much sample 68.

Following the evacuation of the sample collection conduit 6 of any sample therein, the sample collection conduit 6 may be moved from the first position, shown in FIG. 7E, into an intermediate position, as shown in FIG. 7F. In this intermediate position 7F, the plunger 8 is advanced to a position beyond the air vent 30 such that sample collection chamber 16 is closed thereby securely containing the sample 68 within the sample collection chamber 16. Additionally, the sample collection conduit 6 is advanced to a position in which the first conduit 42 and second conduit 44 are sealed against the seal 41. As shown, in the intermediate position the first conduit 42 is free of any sample therein, but the second conduit 44 is filled with sample 68 as the outlet 48 of the second conduit 48 is now below the maximum fill level 28, which in this depicted example the sample 68 is filled up to. The sample collection conduit 4, and thus the plunger 8, may be held in this intermediate position by the intermediate position fixing means 22 described previous with respect to FIG. 3.

Figures 8A, 8B, 8C:
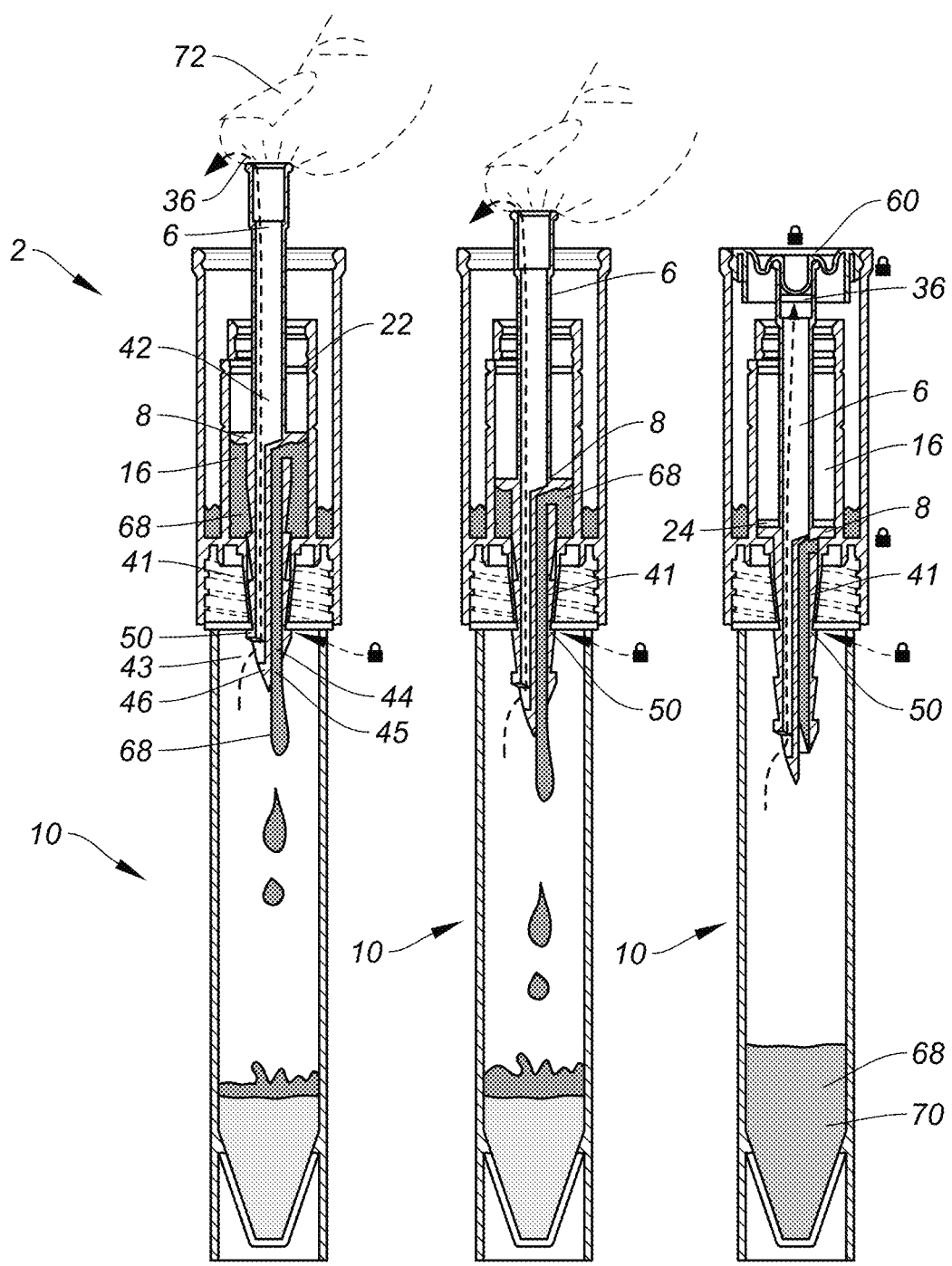
FIGS. 8A-8C show the expelling of a sample from the sample collection chamber into the sample analysis chamber.

If desired, the user may then expel the sample 68 from the sample collection chamber 16 into the sample analysis chamber 10, or indeed into any other component or onto any other device as required. Expelling of the sample into the sample analysis chamber 10 is shown in FIGS. 8A-8C. With reference to FIG. 8A, the sample analysis chamber 10 may comprise a stabilization buffer 70, e.g. UTM®, which is present inside the sample analysis chamber 10 prior to the introduction of the sample 68. In order to expel the sample 68 out of the second end of the sample collection chamber 16, a user may first advance the sample collection conduit 6 into the sample collection chamber 16, e.g. by pushing on the sample collection conduit using their thumb 72. This may require the user to overcome the intermediate position fixing means 22 which may require the user to apply a force greater than a threshold force.

As shown in FIG. 8A, as the sample collection conduit is moved past its intermediate position, towards a second position, the pointed end 46 of the sample collection conduit 6 may break, e.g. perforate, the seal 41 such that the pointed end 46 of the sample collection conduit 6 can pass through the seal 41 into the sample analysis chamber 10.

The seal 41 forms a plurality of pawls which engage with the teeth 50 on the sample collection conduit 41 when it is broken. This interaction thus forms a ratchet arrangement which prevents the sample collection conduit 6 from being retracted once it has been advanced into the sample collection chamber 16. Once the sample collection conduit 6, specifically the second conduit 44 is in fluid communication with the sample analysis chamber 10, the sample contained therein is free to be expelled into the sample analysis chamber 10 by the action of the plunger 8. Additionally, the first conduit 42 puts the sample analysis chamber 10 in fluid communication with the outside of the device 2 via the inlet 36. Accordingly, the first conduit 42 may thus function to relieve balance the pressure within the sample analysis chamber 10 as the sample 68 is inserted therein. As shown, the sample 68 may fall from the second conduit 44 down into the sample analysis chamber and mix with the stabilization buffer.

In order to ensure that the sample can freely drain from the second conduit 44, into the sample analysis chamber 10, without flowing back up through the first conduit, an opening 42 of the first conduit 42 may be arranged above the opening 45 of the second conduit 44.

FIG. 8B shows the sample collection conduit 6 advanced further into the sample collection chamber 16, such that the plunger 8 has forced more of the sample 68 into the sample analysis chamber 10. As shown, as the sample collection conduit 6 is advanced, it is prevented from being retracted through the interaction between the teeth 50 and the seal 41 which acts a pawl.

FIG. 8C shows the device 2 wherein the sample collection conduit 6, and hence the plunger 8, has been fully advanced into the sample collection chamber 16, into a second position, such that all of the sample 68 has been expelled into the sample analysis chamber 10. As shown, the sample 68 and the stabilization buffer 70 may be fully mixed at this point. This may happen naturally as the sample 68 drops into the sample analysis chamber 10 or it may also be assisted through agitation, e.g. shaking, of the device 2 as a whole. In the second position, the sample collection conduit 6 is held within the device 2 by a number of different interactions. Firstly, the sample collection conduit 6 is held in the second position through the interaction of the seal 41, acting as a pawl, and the teeth 50 on the sample collection conduit 6. This interaction forms a ratchet arrangement and prevents the sample collection conduit 6 from being retracted. Further, the sample collection conduit 6 is held in the second position by the second fixing means 24 which engages with the plunger 8 and prevents the plunger 8, and hence the sample collection conduit 6, from moving within the sample collection chamber 16. Additionally, as shown in FIG. 8C, the cap 60 may be attached which may interact with the inlet 36 of the sample collection conduit 6 which may further prevent movement of the sample collection conduit 6. This may thus provide a 'triple lock' for securing the sample collection conduit 6 in place. The cap 60 also serves to block the sample collection conduit 6, specifically the first conduit 42, such that sample 68 cannot escape the device 2. Operation of the cap 60 will be described in more detail below with reference to later Figures.

Figure 9:
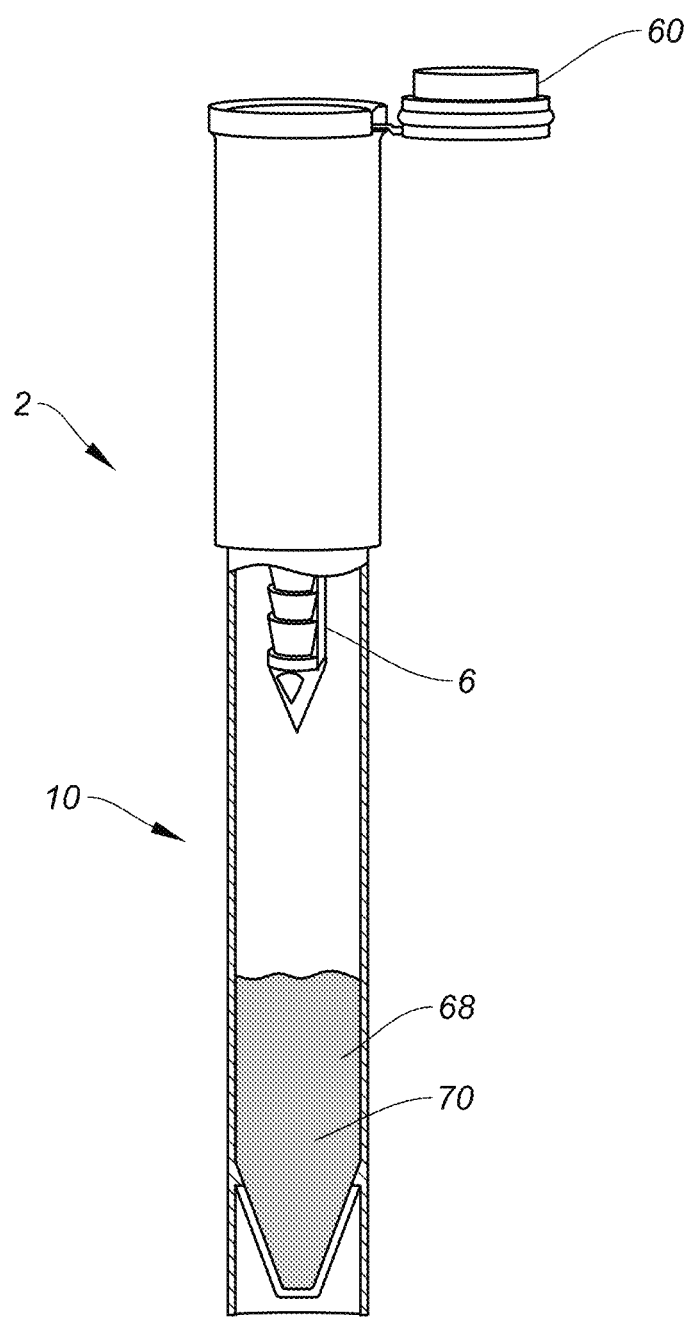
FIG. 9 shows an isometric view of the sample collection device with the sample fully transferred into the sample analysis chamber.

FIG. 9 shows a perspective view of the sample collection device, with the sample collection conduit 6 in the second position, but prior to the attachment of the cap 60. As shown, the sample collection conduit 6 extends into the sample analysis chamber, and the sample 68 and stabilization buffer 70 is mixed together in the sample collection chamber 10.

Figure 10:
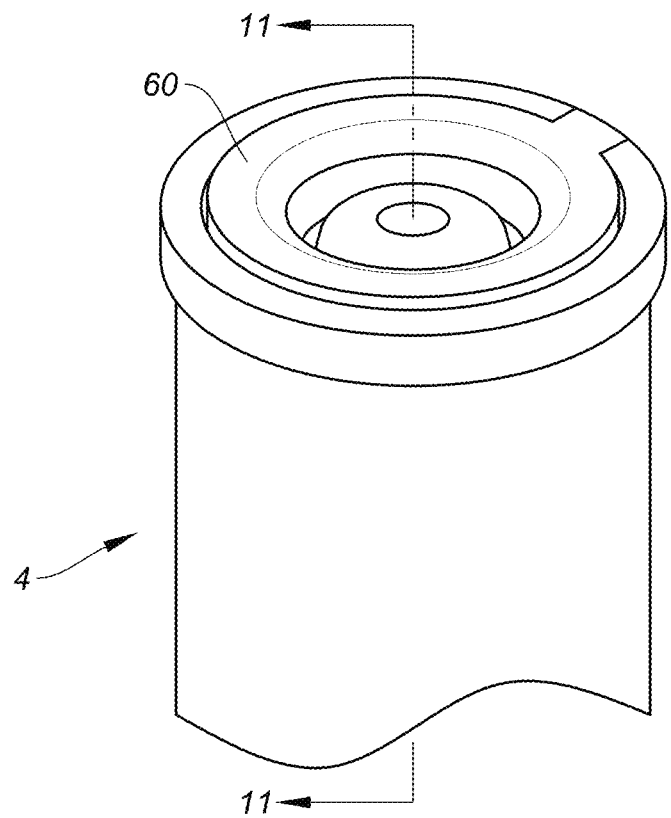
FIG. 10 shows a cap closing the sample collection part.

FIG. 10 shows an isometric view of the cap 60 closing the sample collection part 4. In this Figure, the cap 60 is in a fully closed position in which it cannot be moved out of its closed position and therefore a user cannot gain access to the sample contained within the device 2.

Figure 11:
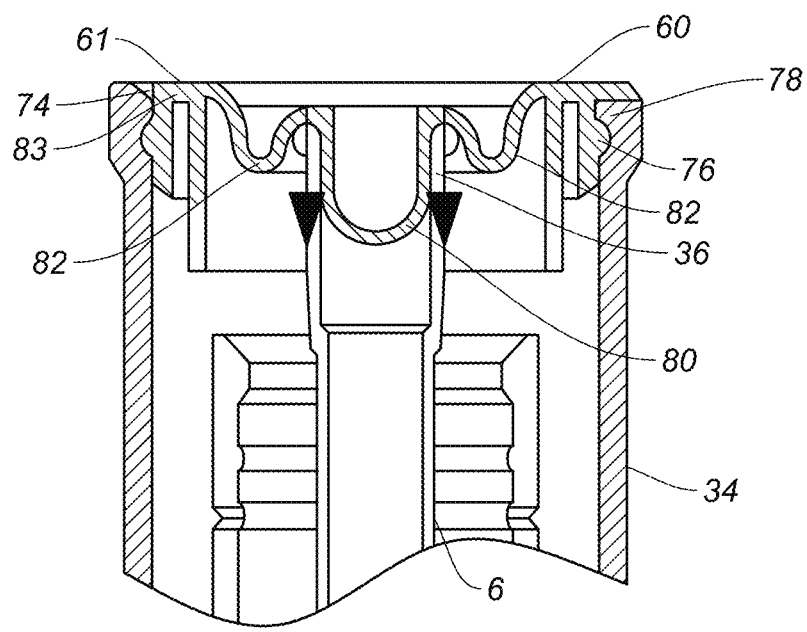
FIG. 11 shows a side sectional view of the cap closing the sample collection part.

FIG. 11 shows a side cross-sectional view of the cap 60 when fully inserted. When in the fully inserted position, the top 61 of the cap is at the same level as the top 74 of the outer wall 34 of the sample collection part 4. This makes it difficult for a user to remove the cap 60 as there is nowhere for a user to get a grip on the cap 60. The cap 60 may even be configured such that the top 61 of the cap 60 is below the top 74 of the sample collection part 4.

When in the closed position as shown in FIG. 11, the cap 60 is held in place by the engagement of a circumferential rim 76 on the cap 60 with a circumferential recess 79 on the outer wall 34 of the sample collection part 4. Further, the cap 60 comprises a conduit sealing portion 80 configured to seal the sample collection conduit 6. The conduit sealing portion 80 is shaped to seal in the inlet 36 of the sample collection conduit 6. The inlet 36 may comprise a tapered surface such that when inserted the conduit sealing portion 80 and inlet form a friction fitting. This friction fitting may act to hold the cap 60 in place in the closed position. The conduit sealing portion 80 may be resiliently biased into a sealing position, as shown, by a resilient portion 82. The resilient portion 82 effectively forms a spring which biases the conduit sealing portion 80 into the inlet 36. In the embodiment shown, the resilient portion 82 has an annular shape and connects the sealing portion 82 to a peripheral portion 83 of the cap 60. The resilient bias may be provided by the inherent resiliency of the material of the cap 60, which may be plastic, and the shape of the sealing portion 82, which has an 'S' shape in the embodiment shown. Whilst the conduit sealing portion 80 is shown as sealing into the inlet 36, it could of course seal around the inlet 36, or be omitted entirely.

FIG. 12A shows an isometric view of the conduit cap 14 in isolation. The conduit cap 14 is in the form of a hollow cylinder closed at one end and with an opening 85 at the other end. The conduit cap 14 comprises an end stop 84 in the form of a circumferential protrusion, as well as an external rim 84. The end stop 84 is arranged to limit how far the conduit cap 14 can be attached the sample collection part 4 as will be shown more clearly in later Figures. FIG. 12B shows the conduit cap 14 in side view with an outer wall thereof transparent such that the inner components are visible. As shown in this Figure the conduit cap 14 comprises a plurality of fins 18 arranged to receive the sample collection conduit 6 in use. The arrangement of the fins 18 can be seen more clearly in FIG. 12C which shows an end-on view of the conduit cap 14 when viewed through the opening 85. The fins 88 are arranged in a circular arrangement to define a circular void 89, in the middle of the fins 88, for receiving the sample collection conduit 6.

FIG. 13A shows an isometric view of the storage cap 12. As shown, the storage cap 12 comprises an external thread 90 for use in attaching the transport cap 12 to the sample collection part 4. The transport cap further comprises a seal receiving portion 92 configured to receive the seal 41 on the sample collection part 4. The seal receiving portion 92 may act to protect the seal 41 and prevent it from breaking until it is desired to do so. The bottom rim 94 of the storage cap 12 is flat and level such that the storage cap 12, and the sample collection part 4 if attached thereto, can stand vertically on a surface. FIG. 13B shows a cut-away view of the storage cap 12 shown in FIG. 13A. As visible in this view, the seal receiving portion 92 has a conical 96 recess for receiving the conically shaped seal 41. Of course, the seal receiving portion 92 may have any shape which corresponds to the shape of the seal 41.

Figures 14A, 14B:
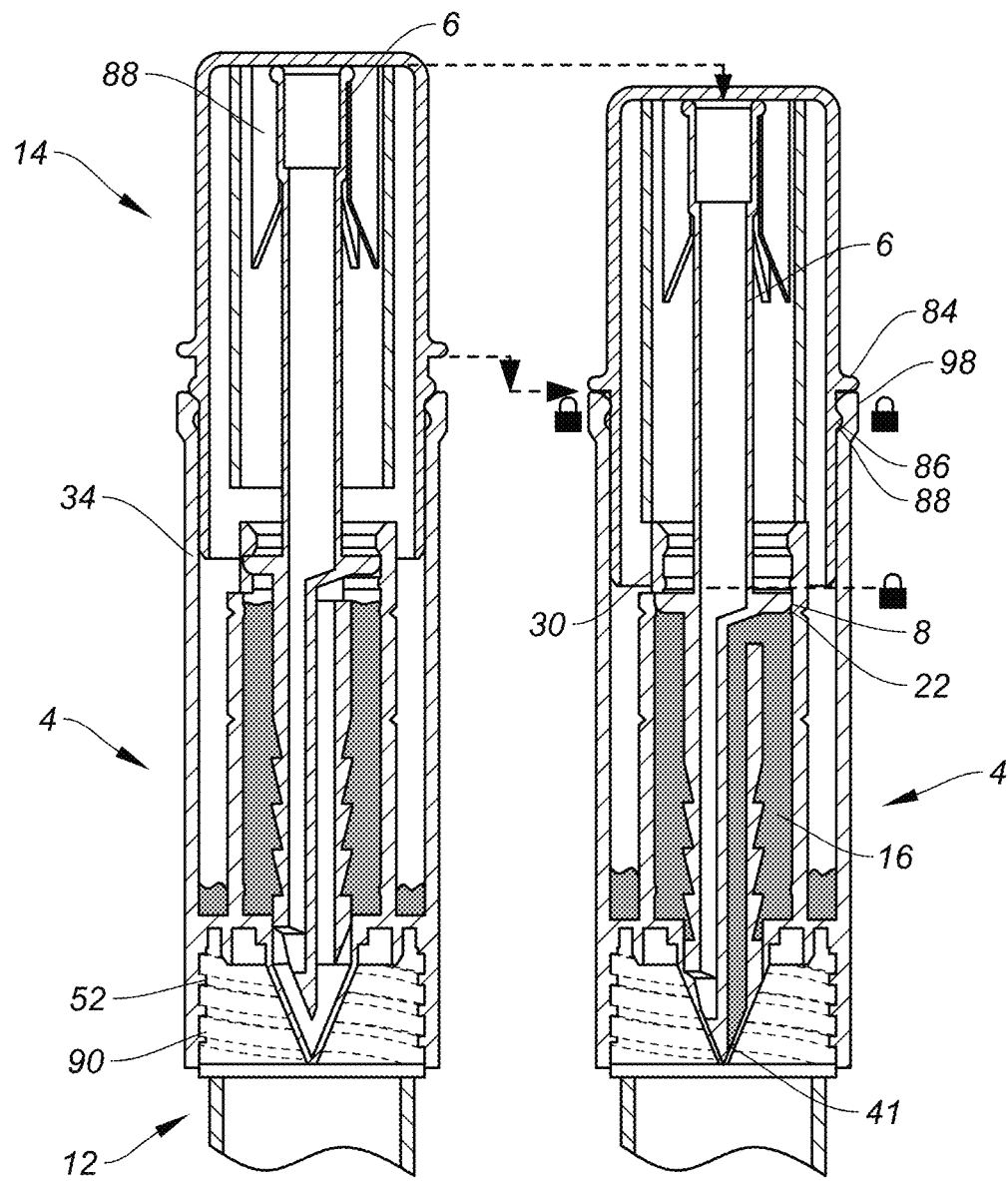
FIGS. 14A and 14B show the application of the secondary cap shown in FIGS. 12A-12C.

FIG. 14A shows a side sectional view of the sample collection part 4 with the storage cap 12 attached thereto, as well as with the conduit cap 14 partially attached. The storage cap 12 is attached to the sample collection part 4 by engagement between the outer thread 90 and the internally threaded collar 52. In FIG. 14A, the secondary cap 14 is partially inserted into the outer wall 34 of the sample collection part 4. In this position, the fins 88 receive the sample collection conduit 6. The fins 88 act to guide the sample collection conduit 6 within the conduit cap 14 so as to obtain precise control over the sample collection conduit 6 as it is inserted into the sample collection chamber 4.

In order to close off the sample collection chamber 16, the sample collection conduit 6, and thus the plunger 8 may be advanced into the sample collection chamber 16 by pushing the conduit cap 14, which pushes the sample collection conduit 6. This is demonstrated in FIG. 14B in which the conduit cap 14 has been pushed into the sample collection part 4 to the point at which the end-stop 84 engages against an upper rim 98 of the sample collection part 4. This engagement stops the conduit cap 14 from being advanced any further.

Once the conduit cap 14 is in the illustrated position, the sample collection conduit 6 is in an intermediate position in which the plunger 8 is below the air vent 30, thereby sealing the sample collection chamber 16. The conduit cap 14 may thus be used to push the sample collection conduit 6 into the sample collection chamber 16. Additionally, the first and second conduits 42, 44 are moved into a sealing position with the seal 41 such that fluid cannot flow therethrough. In this position, fluid cannot flow between the first and second conduits 42, 44. This therefore acts to fully seal the sample collection chamber 16. The sample collection conduit 6 is held in this intermediate position by the intermediate fixing means 22 as well as the conduit cap 14 whilst it is attached. The secondary cap 44 is held in place through engagement of the external rim 86 within the circumferential recess 88. The sample may thus be transported safely within the sample collection part 4.

Figure 15:
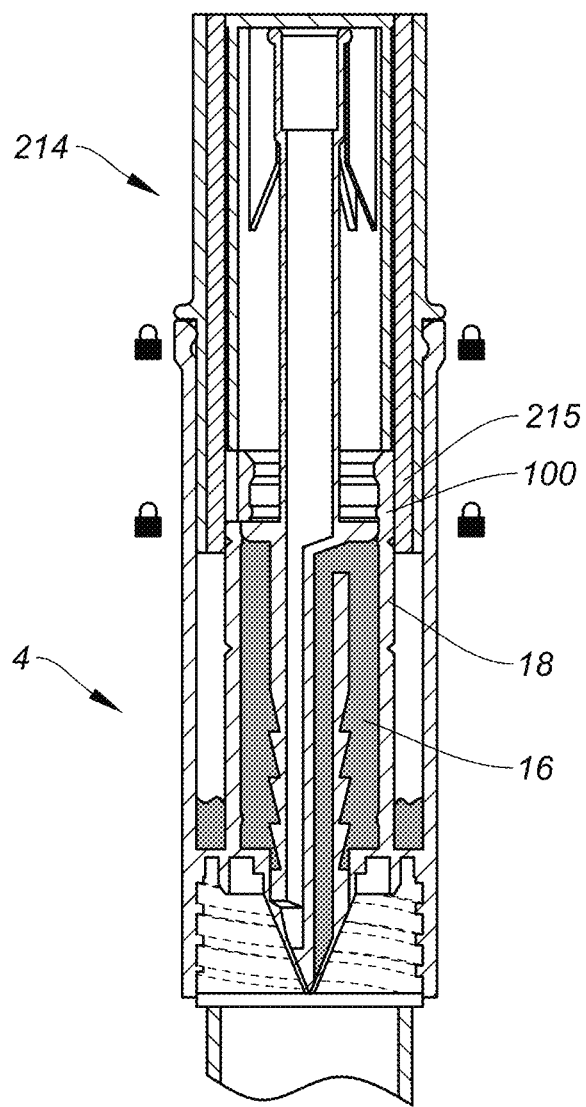
FIG. 15 shows an alternative secondary cap in cross-sectional view attached to the sample collection part.

FIG. 15 shows a side sectional view of another embodiment of a conduit cap 214 attached to the sample collection part 4. The conduit cap 214 is identical to the conduit cap 14 shown in earlier Figures, and functions in an identical manner, except that conduit cap 214 comprises an elongate sealing portion 215 which extends so as to seal around an upper part 100 of an outer wall 18 of the sample collection chamber 16.

FIG. 16A shows an isometric view of another embodiment of a sample analysis chamber 310. As with the first embodiment shown in earlier Figures, the sample analysis chamber 310 comprises an external thread 311 at one end thereof for connecting the sample analysis chamber 310 to the sample collection part 4. FIG. 16B shows a side view of the sample analysis chamber 310 with an outer wall transparent such that the internal parts thereof can be seen. As illustrated in this Figure, the sample analysis chamber 310 comprises a conduit seal 313 arranged within the sample analysis chamber which is supported by a support wall 315. The support wall 315 defines an annular space 317 in which the sample may collect. The conduit seal 313 is conically shaped for receiving the corresponding shaped pointed end of the sample collection conduit 6 shown in earlier Figures.

Figure 17:
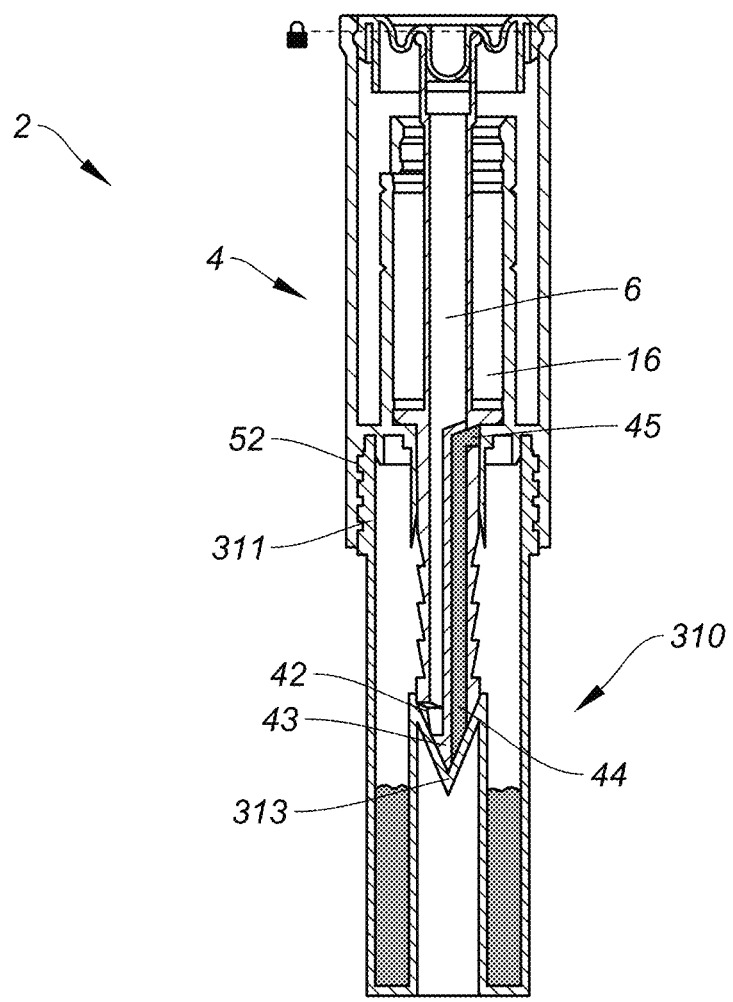
FIG. 17 illustrates the use of the sample analysis chamber shown in FIGS. 16A-16B.

FIG. 17 shows a side cross-sectional view of the device 2 with the sample analysis chamber 310 connected to the sample collection part 4 connected through engagement of the external thread 311 with the internally threaded collar 52. In the view shown, the sample collection conduit 6 is in the second position, as shown in earlier Figure. In this embodiment, in the second position, the lower end 43 of the sample collection conduit 6 engages into the conduit seal 313 such that the first conduit 42 and second conduit 44 are sealed by the conduit seal 313. As the sample collection conduit 6 is sealed around the opening 45 at the bottom of the sample collection chamber 16, the sealing of the first and second conduits 42, 44 acts to seal the sample analysis chamber 310.

Figure 18:
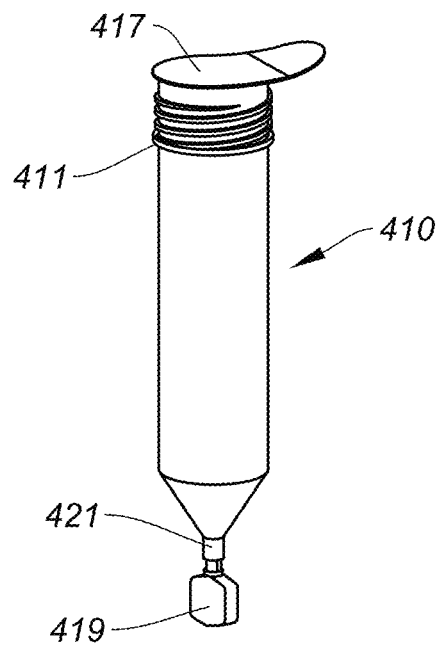
FIG. 18 shows a perspective view of a dispense chamber.

FIG. 18 shows an isometric view of a dispense chamber 410 which may be attached to the sample collection part 4 shown in earlier Figures. The dispense chamber 410 comprises an external thread 411 at one end thereof for securing the dispense chamber 410 to the sample collection part 4 as described below with respect to FIG. 19. The dispense chamber further comprises a removable cover 417 which acts to seal the dispense chamber 410 prior to use. This removable cover 417 may be removed prior to connection of the dispense chamber 410 with the sample collection part 4.

The dispense chamber 410 further comprises a dispense outlet 421 through which a sample 68 may be dispensed from. The dispense outlet 421 may be dimensioned such that the sample 68 only passes out of the dispense chamber 410 when the dispense chamber 410 is squeezed. A removable seal 419 closes the dispense outlet 421 until a user is ready to dispense the sample 68.

Figure 19:
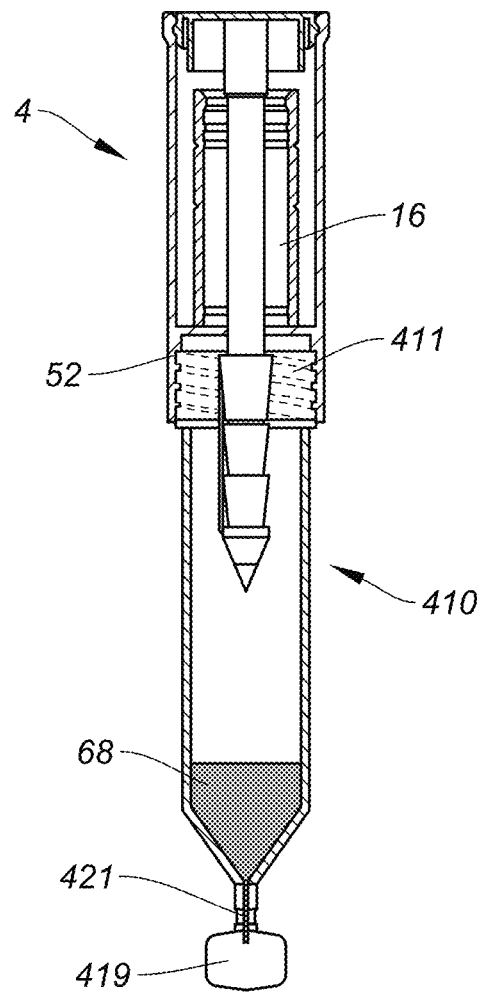
FIG. 19 shows the dispense chamber attached to the sample collection part.

FIG. 19 shows a side sectional view of the sample collection part 4 with the dispense chamber 410 attached thereto. As shown, the dispense chamber 410 is connected to the sample connection part through engagement of the outer external thread 411 with the internally threaded collar 52. In the configuration shown in FIG. 19, the sample 68 has been expelled from the sample collection chamber 16 into the dispense chamber, in an identical manner to that described above with respect to earlier Figures. Once within the dispense chamber, the sample 68 is contained therein by the removable seal 419 which closes the dispense opening 421.

Figure 20:
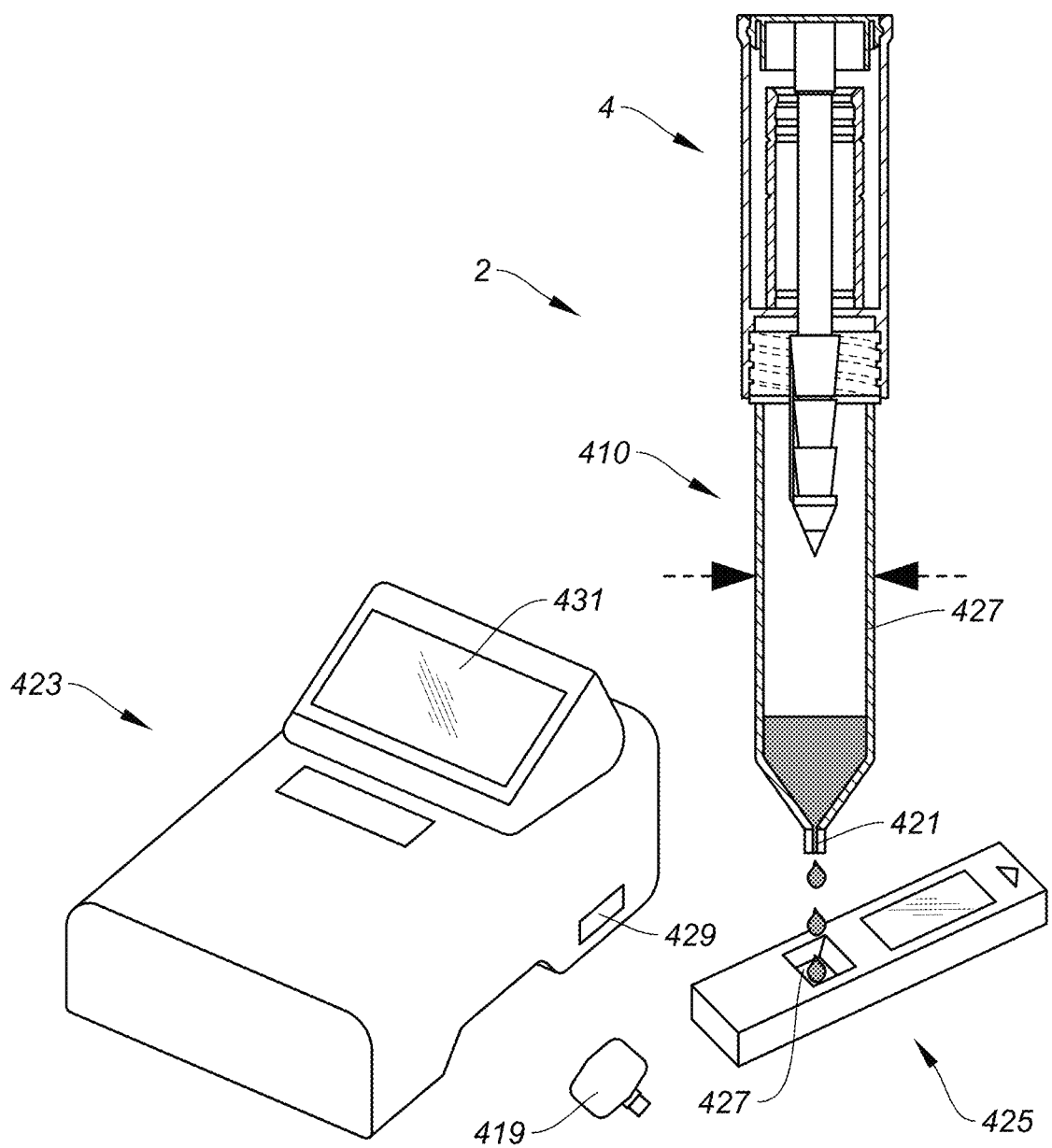
FIG. 20 shows the sample collection device shown in FIG. 19 in combination with a sample analysis machine.

FIG. 20 illustrates how the device 2 may be used with a sample analysis machine 423. Using the device 2, with the dispensing chamber 410 attached to the sample collection part 4, and with the sample expelled into the dispensing chamber 410, a user may first remove the removable seal 419. This may be achieved, for example, by twisting the removable seal 419 relative to the dispensing chamber 410. Once seal 419 is removed, the dispense outlet 421 will then be open. The dispense outlet 421 may be dimensioned such that the sample does not leave the dispense outlet 421, unless it is forced out, e.g. by squeezing of the dispense chamber 410, specifically by compressing an outer wall 427 of the dispense chamber 427. This arrangement may allow for controlled dispensing of the sample, for example on drop-by-drop basis. The sample may be dispensed from the dispense chamber 410, via the dispense outlet 421, onto a sample analysis tray 425, specifically onto a sample receiving section 427. Once the sample has been dispensed onto the sample receiving section 427, the sample analysis tray 425 may be inserted into a slot 429 on the sample analysis machine 423. Analysis of the sample may then be performed and results of the analysis may be displayed on a display 431.

Figure 21:
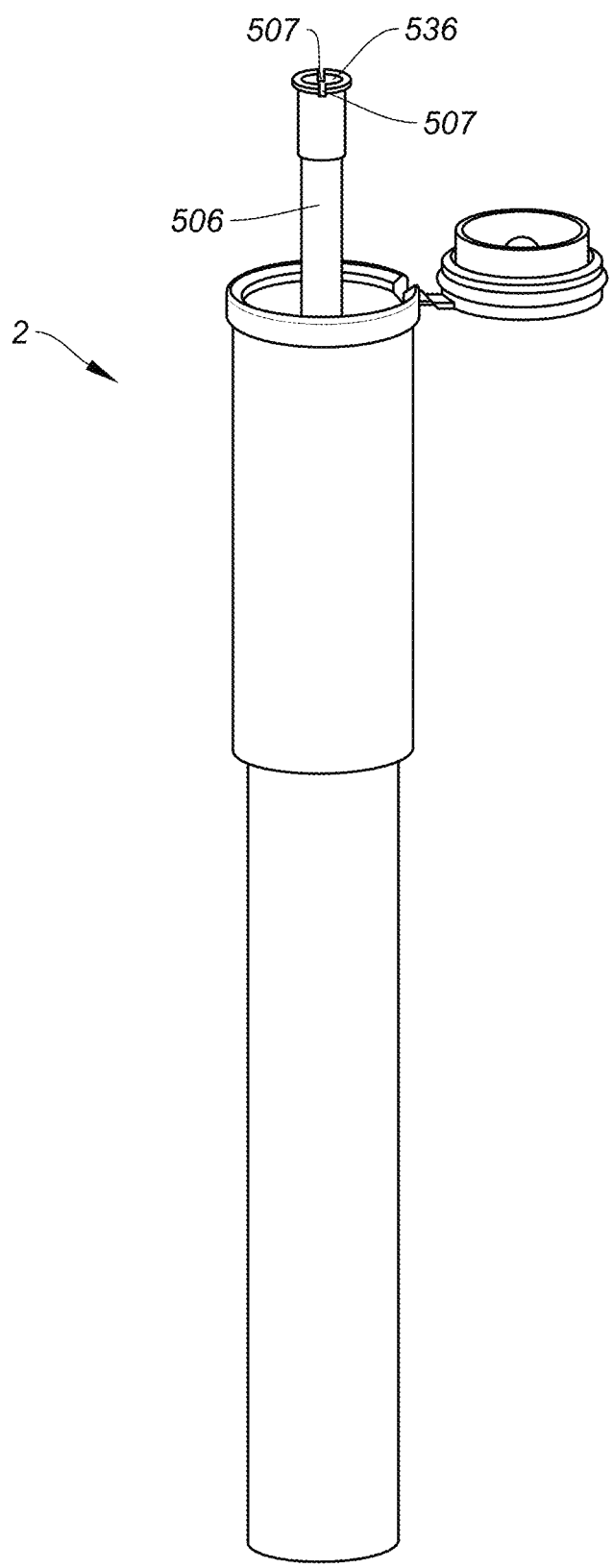
FIG. 21 shows a perspective view of a sample collection device with a sample collection conduit comprising an air vent therein

FIG. 21 shows a perspective view of a sample collection device 2 with an alternative sample collection conduit 506 arranged therein. The sample collection conduit 506 comprises air vents 507 arranged at the inlet 536 of the sample collection conduit 506. As will be appreciated, when the sample collection conduit 536 is pushed into the device 2, a user's thumb, or another surface, in some positions may close of the inlet 536. Accordingly, in this instance, the air vents 507 may allow any air, e.g. from the sample analysis chamber or another component connected to the device 2, to vent through the sample collection conduit 506 and out through the air vents 507. This may, therefore, allow the sample collection conduit 506, and the plunger (not visible in this Figure), to be more easily inserted into the device 2 as there may be no build-up of air pressure.

Figure 22:
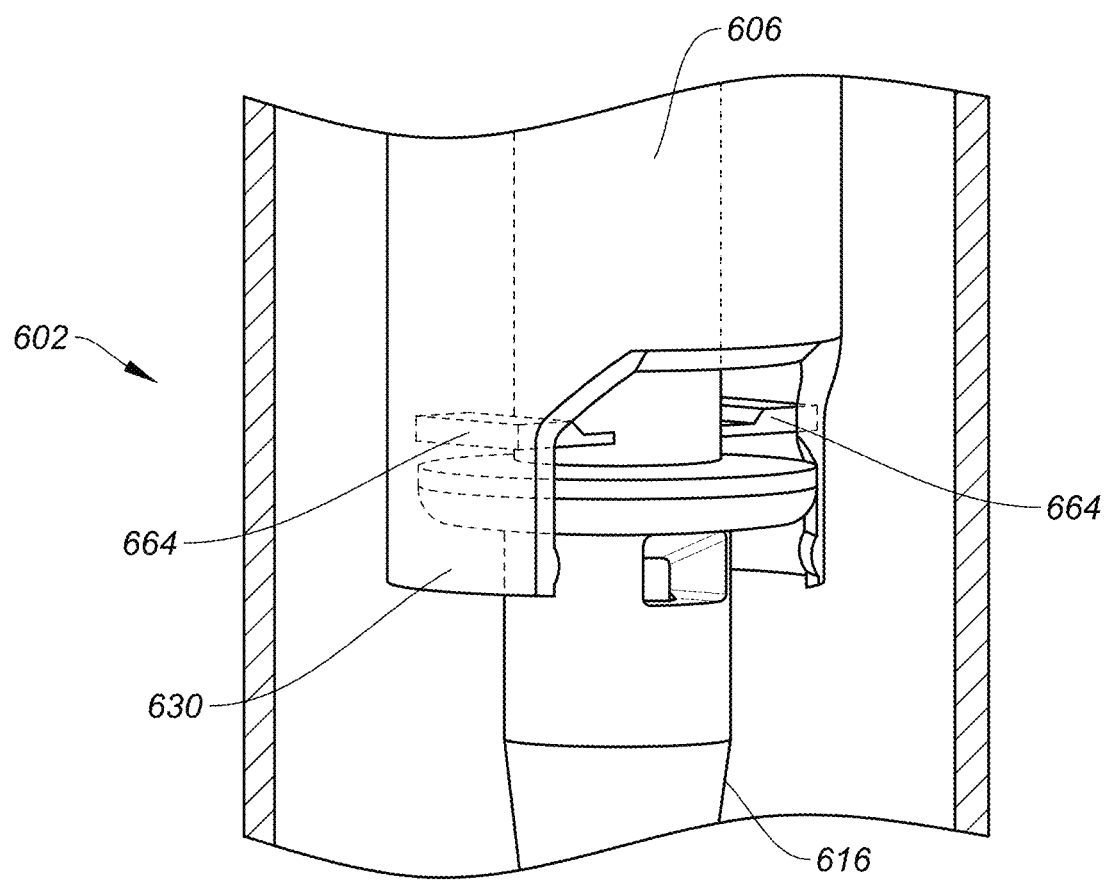
FIG. 22 shows an isometric view of a sample collection device in accordance with another embodiment of the present invention.
Figure 23:
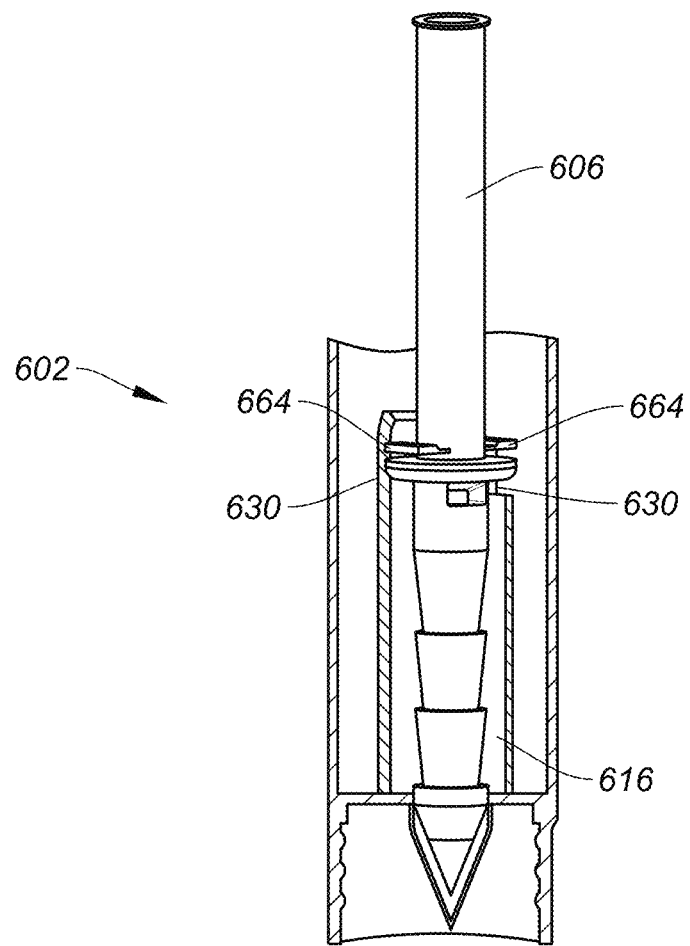
FIG. 23 shows a partial cut-away view of the sample collection device shown in FIG. 22

FIG. 22 shows a perspective view of another embodiment of a sample collection device 602, with the walls of the device 602 shown as transparent to reveal the inner parts of the device 602. FIG. 23 shows a partial cut-away view of the device 602 shown in FIG. 22. With reference to FIGS. 22 and 23, in this illustrated embodiment, the sample collection conduit 606 is guided within the device 602 for at least part of its range of linear motion. As shown, the sample collection conduit 606 comprises two protrusions 664 extending radially away from a main body of the sample collection conduit 606. The two protrusions 664 are arranged and dimensioned to sit within the air vents 630 arranged at the top of the sample collection chamber 616. In this regard, the air vents 630 not only function to allow air to escape the sample collection chamber 616 and allow any excess sample to overflow the sample collection chamber 616, the air vents 630 also function together with the protrusions 664 to form the guide arrangement. As will be appreciated, when the protrusions 664 are received within the air vents 630, the sample collection conduit 606 cannot be rotated.

When the protrusions 664 abut against a lower end of the air vents 630, when desired, the sample collection conduit 606 may be pushed into the device 602 with sufficient force such that the protrusions 664 flex upwards and towards the sample collection conduit 606. At this point, the protrusions 664, and hence the sample collection conduit 606, may be advanced past the air vents 630 and further into the device 602. Once past the air vents 630, the protrusions 664 will no longer be received by the air vents 630, or any other form of guiding means, and the sample collection conduit 606 may then be free to rotate within the device 602. This may be acceptable as once advanced into this position, the air vents 630 may no longer be in fluid communication with the sample within the sample collection chamber, and the thus risk of any sample leaving the sample collection conduit 606, bypassing the sample collection chamber 616 and passing out through the air vents 630 will no longer be present.

Figure 24:
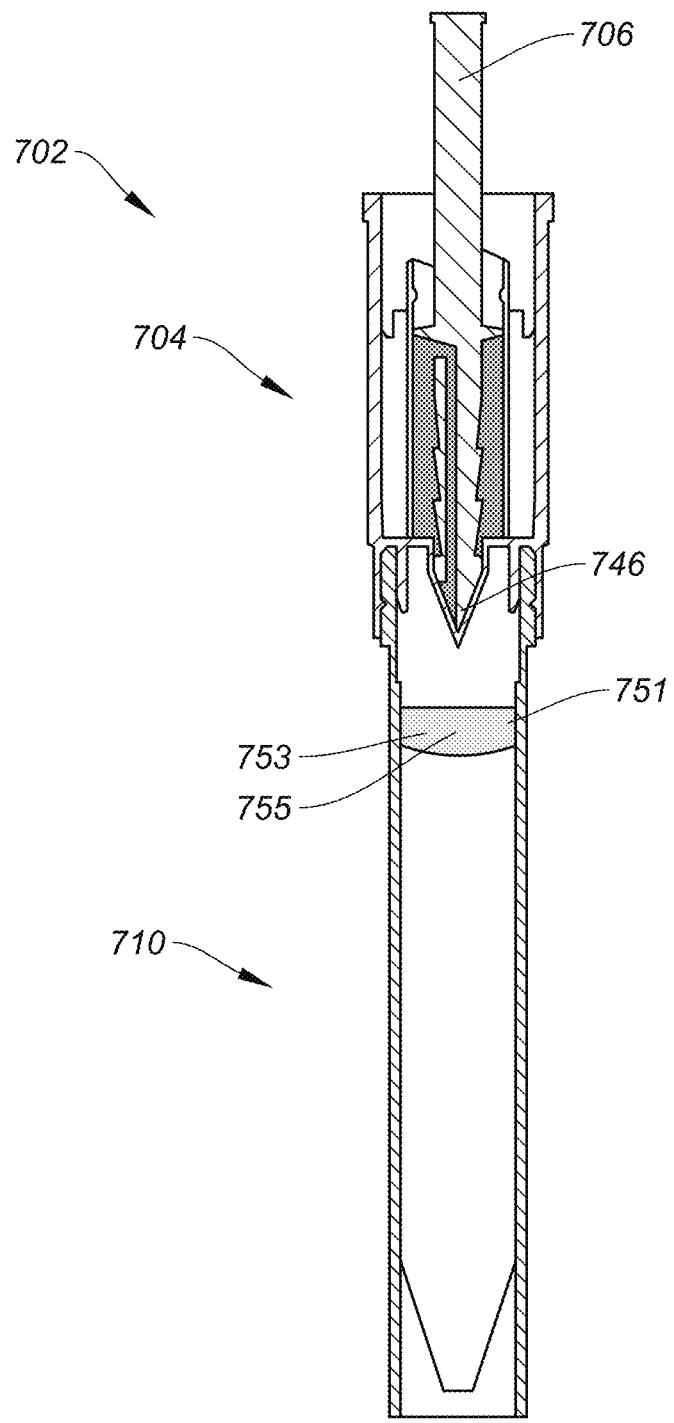
FIG. 24 shows a cross-sectional view of a sample collection device in accordance with another embodiment of the present invention which comprises a reagent contained within a capsule in the sample analysis chamber.

FIG. 24 shows a cross sectional view of another embodiment of a sample collection device 702. The sample collection device 702 comprises a sample collection part 704 which functions in an identical manner to the sample collection device 2 described above. The sample collection device 702 further comprises a sample analysis chamber 710 which is configured to be attached to the sample collection part 704. In the view shown in FIG. 24, the sample analysis chamber 710 is connected to the sample collection part 704. The sample analysis chamber 710 comprises a capsule 753 arranged within the sample analysis chamber 710. The capsule 753 contains a reagent 755. The capsule 753 is supported within the sample analysis chamber on an internal circumferential rim 751. Of course, any other suitable means for supporting the capsule 753 may be used. As will be appreciated by those skilled in the art, the capsule 753 may be shaped so as to engage with the rim 751 and rest thereon. The sample collection device 702 may function in a similar manner to the embodiments described below, except that only a single reagent 755 is provided, whereas the embodiments described below comprise a plurality of reagents.

FIGS. 25A-25E illustrate cross-sectional views of another embodiment of a sample collection device 802 in use. As depicted in FIG. 25A, the sample collection device 802 comprises a sample collection part 804, which may function in an identical manner to the sample collection device 2 described above. The sample collection device 802 further comprises a sample analysis chamber 810 which is connected to the sample collection device 802, and is thus connected to the sample collection chamber 816 thereof. Similarly to the embodiment described above with respect to FIG. 24, the sample analysis chamber 810 comprises a capsule 853 arranged therein which contains a first reagent 855. Similarly to the embodiment described above in FIG. 24, the capsule 855 is supported within the sample analysis chamber by an internal circumferential rim 851. The sample analysis chamber further comprises a second reagent 857 stored directly in the sample analysis chamber 810. The first reagent 855 and second reagent 857 are prevented from mixing due to the barrier provided by the capsule 853 which contains the first reagent 855. In the state shown in FIG. 25A, the sample 868 is contained within the sample collection chamber 816.

When it is desired to expel the sample 868 into the sample analysis chamber 810, the sample collection conduit 806 may be advanced from the first position shown in FIG. 25A towards a second position in which the sample collection conduit 806 is advanced into the sample collection chamber 816. Initial movement of the sample collection conduit 806 is shown in FIG. 25B. As illustrated in this Figure, as the sample collection conduit 806 is advanced into the sample collection chamber 816, in addition to breaking the seal 841 in a similar manner to the embodiments discussed above, the pointed end 846 of the sample collection conduit 806 also breaks, e.g. perforates, the capsule 853. As a result, the sample 868 which is expelled from the sample collection chamber 816 is then able to mix with the first reagent 855. With the sample collection conduit 806 in the position illustrated in FIG. 25B, the sample collection conduit 806, specifically the pointed end 841 thereof, has not yet broken a lower wall 849 of the capsule 853. Accordingly, the sample 868 and first reagent 855 may mix together, at least partially, before the mixture is able to reach other portions of the sample collection chamber 810.

As shown in FIG. 25C, as the sample collection conduit 806 is advanced further, the pointed end 846 may perforate the lower wall 849 of the capsule 853 and the fluid 859 which is a mixture of the sample 868 and the first reagent 855 is able to flow into the rest of the sample collection chamber 810 towards the second reagent 857.

Once all of the sample 868 has been expelled from the sample collection chamber 816, as depicted in FIG. 25C, the sample collection part 804 may then be separated from the sample analysis chamber 810. This is depicted in FIG. 25D. At this point, the fluid 859 may mix with the second reagent 857 to form a second fluid 861. As the sample collection part 804 is separated from the sample analysis chamber 810, the capsule 853, which no longer contains any of the first reagent 855, or only contains a residue of the first reagent 855, is also withdrawn from the sample analysis chamber 810. As depicted, the teeth 850 on the sample collection conduit 806, which also act as pawls on the sample collection conduit 806 as part of a restriction arrangement which prevents the sample collection conduit 806 from being retracted back into the sample collection chamber 816, also act to engage with and hook onto the capsule 853. The teeth 850 thus form hook portions which hook onto the capsule 853. As a result, when the sample collection part 804 is separated from the sample collection chamber 810, the capsule 853 is also withdrawn from the sample collection chamber 810. This may, advantageously, facilitate further analysis as the capsule 853 will not need to be separately removed. Whilst in the embodiment shown, the teeth 850 engage with and hook onto the capsule 853, any other suitable means may be used to engage and extract the capsule 853.

As depicted in FIG. 25E, with the sample collection part 804 removed, a cap 863 may be placed on the sample analysis chamber 810, for safe storage of the second fluid 861 therein. The sample analysis chamber 810 may then, for example, be transported for analysis. Analysis may be performed on the second fluid 861 within the sample analysis chamber 810, or alternatively, at least a portion of the second fluid 861 may be dispensed onto/into a suitable analysis means.

FIGS. 26A-26J show cross-sectional views of a further embodiment of a sample collection device 902 in use. FIG.

26A illustrates the sample collection device 902 which is similar to the sample collection device 802 described above, except that the capsule 953 containing the first reagent 955 is supported on a support 965 which is arranged within the sample collection chamber 910. The support 965 may have any suitable structure that is capable of holding the capsule 953 in position in the sample collection chamber 910. In the embodiment depicted, the support 965 has a dish-shape, wherein an external rim 945 thereof engages with an internal wall 947 of the sample analysis chamber 910. The sample collection device 902 may be used for the analysis of an oral fluid sample in testing for SARS-CoV-2. As such, the first reagent 955 may comprise a lysis buffer for use in isolating the RNA within the sample 968. The sample analysis chamber 910 further comprises a second reagent 957 arranged therein. The second reagent 957 is prevented from mixing, at least initially, with the first reagent 955, due to the capsule 953 which contains the first reagent 955. In the exemplary case of testing for SARS-CoV-2, the second reagent may comprise magnetic particles, e.g. magnetic nanoparticles which are configured to bind with the RNA. The magnetic particles may be mixed in a solution. The sample collection part 904 of this embodiment functions in an identical manner to the sample collection part 4 described above.

Operation of the sample collection device 902 will now be described with reference to FIG. 26B. As the sample collection conduit 906 is advanced into the sample analysis chamber 916, the pointed end 946 of sample collection conduit 906 perforates the capsule 953 and the sample 968 and first reagent 955 are able to mix. In the case wherein the first reagent 955 comprises a lysis buffer, the mixing of the sample 968 and the first reagent 955 results in the separation and isolation of the RNA within the sample 968. Referring to FIG. 26C, as the sample collection conduit 906 is advanced further, the pointed end 946 thereof also breaks the support 965. As a result, the first fluid 959, which is the result of the mixing of the first reagent 953 with the sample 968, is then free to fall towards the second reagent 957.

As depicted in FIG. 26D, the sample collection part 904 may be separated from the sample analysis chamber 910. The teeth 950 on the sample collection conduit 906 engage and hook onto the capsule 953 and support 965 and as a result the capsule 953 and support 965 are withdrawn from the sample analysis chamber 910 when the sample collection part 904 is separated therefrom. The first fluid 959 may mix with the second reagent 957 to form a second fluid 967. In the exemplary case whereby the second reagent comprises magnetic nanoparticles, the magnetic nanoparticles may bind with the RNA in the fluid 959, and form the second fluid 967.

In this case, a magnetic field may then be used to separate the magnetic nanoparticles, which are bound to the RNA, from the rest of the second fluid 967. This is illustrated in FIG. 26E, wherein a magnetic device 969 is brought into proximity of the sample analysis chamber 910 to apply a magnetic field thereto. In the embodiment depicted, the magnetic device 969 may engaged with, e.g. attached to, the sample analysis chamber 910. This may be achieved by any suitable means, for example a press-fitting operating between the magnetic 969 and the sample collection chamber 910. The magnetic device 969 may be a permanent magnet which provides a permanent magnetic field, or an electromagnet capable of selectively producing a magnetic field. As illustrated, with the magnetic device 969 connected to the sample collection chamber 910, the magnetic nanoparticles 957 which form part of the second reagent, with the RNA bound thereto, are drawn towards the magnetic device 969 when it applies a magnetic field.

At this point, the remainder of the second fluid 967 may be separated from the magnetic nanoparticles 957, and the RNA which is bound thereto, which are held by the magnetic device 969. This is illustrated in FIG. 26F. In FIG. 26G, a third fluid 971 may be added to the sample analysis chamber 910. The third fluid 971 may be a cleaning fluid, e.g. an alcoholic fluid, suitable for washing the nanoparticles 957 and the RNA bound thereto. Following this washing, in the step illustrated in FIG. 26H, the third fluid 971 may be separated from the magnetic nanoparticles 957 and RNA, for example by emptying the sample collection chamber 910, with the magnetic device 969 still attached, thus retaining the magnetic nanoparticles 957.

As illustrated in FIG. 26I, a fourth fluid 973 may be added to the sample collection chamber 910, and an elution process may be employed to separate the RNA from the magnetic nanoparticles 957. As a result, the RNA may then be contained within the fourth fluid 973 and no longer be bound to the magnetic nanoparticles 957. Advantageously, throughout this process, the RNA from the sample has not yet been removed from the sample analysis chamber 910, and thus the risk of contaminating the sample may be significantly reduced.

With the magnetic device 969 still attached to the sample analysis chamber 910, the fourth fluid 973, which comprises the RNA, may be dispensed from the sample analysis chamber 910. This fourth fluid 973 may be transferred onto any suitable means for analysis of the RNA contained within the fluid 973. The sample collection device 902 described above provides an efficient and clean means for processing a sample 968, particularly for processing and extracting RNA from a sample 968.

In the embodiment described above, the magnetic device 969 is depicted as a disk-shaped magnetic device which is attached to the sample analysis chamber 910. However, this is just for explanatory purposes and the magnetic device 969 may have any shape and form suitable for applying a magnetic field to the sample analysis chamber. For example, the magnetic device 969 may wrap around the sample analysis chamber 910 along its length, rather than being attached to a bottom portion of the sample analysis chamber 910. Additionally, the magnetic device 969 may be part of an apparatus, which is not illustrated, which may process, and optionally analyze, the sample 968.

FIG. 27A-27F show cross-sectional views of another embodiment of sample collection device 1002. The sample collection device 1002 comprises a sample collection part 1004 which functions in an identical manner to the sample collection part 2 described above. The sample collection device 1002 further comprises a sample analysis chamber 1010 attached to the sample collection part 2. The sample collection chamber 1010 comprises a first reagent 1055, a second reagent 1075 and a third reagent 1057. The type of each reagent may depend on the type of analysis which is to be performed on the sample 1068. Unlike earlier embodiments wherein at least one of the reagents was contained within a capsule, in the embodiment of FIG. 27A, the sample collection chamber 1010 comprises a first partition 1065 separating the first reagent 1055 and the second reagent 1075. The sample collection chamber 1010 also comprises a second partition 1077 separating the second reagent 1075 from the third reagent 1057. The first and second partitions 1065, 1077 may comprise any suitable structure for separating the reagents and may act to define separate sub-chambers, e.g. three sub-chambers, within the sample analysis chamber 1010.

Operation of the sample collection device 1002 will now be described, first with reference to FIG. 27B. As depicted, as the sample collection conduit 1006 is advanced into the sample collection chamber 1016, the pointed end 1046 of the sample collection conduit 1006 breaks the seal 1041 and the sample 1068 begins to be expelled into the sample analysis chamber 1010. At this position, the sample collection conduit 1006 has not yet broken the first partition 1065 and thus the sample 1068 mixes with the first reagent 1055.

Figures 27A, 27B, 27C:
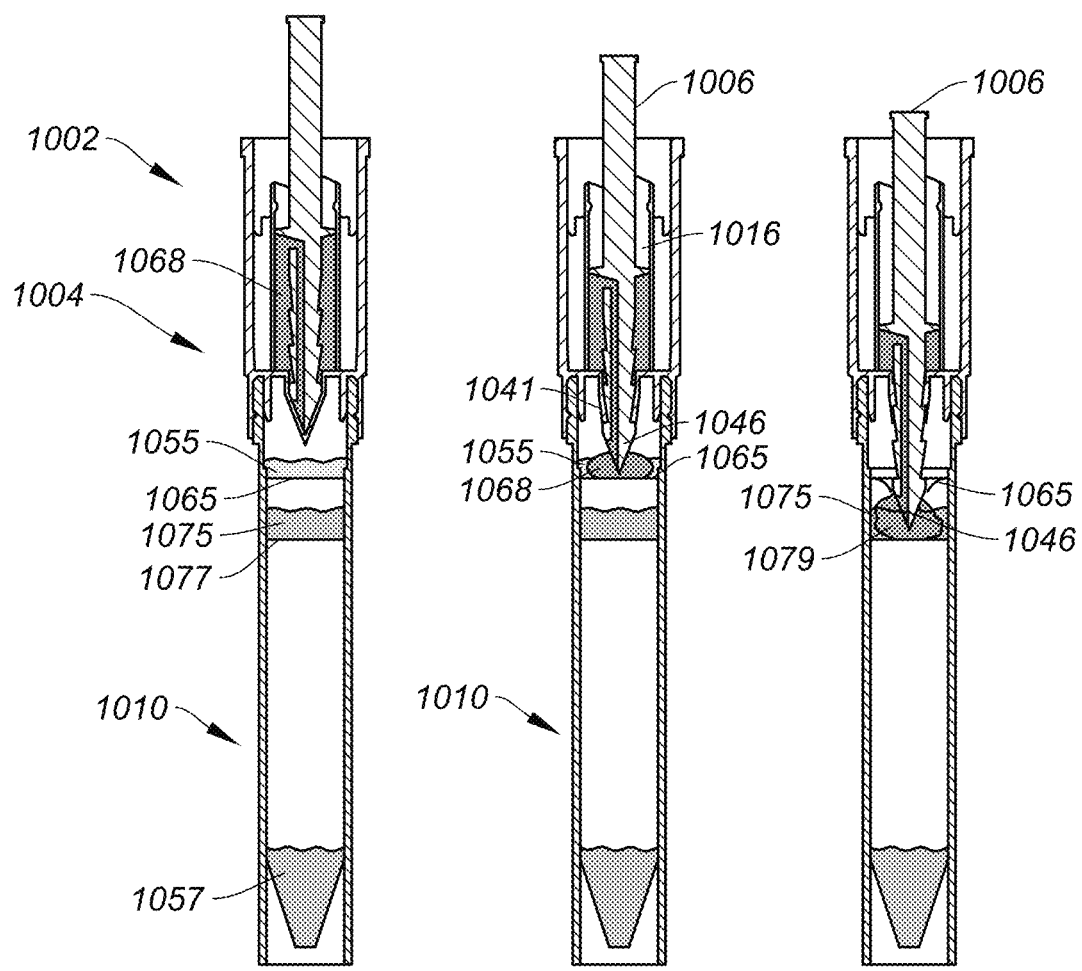
FIGS. 27A-27F show cross-sectional views of sample collection device in accordance with another embodiment of the present invention which comprises three reagents separated within the sample analysis chamber by partitions.
Figures 27D, 27E, 27F:
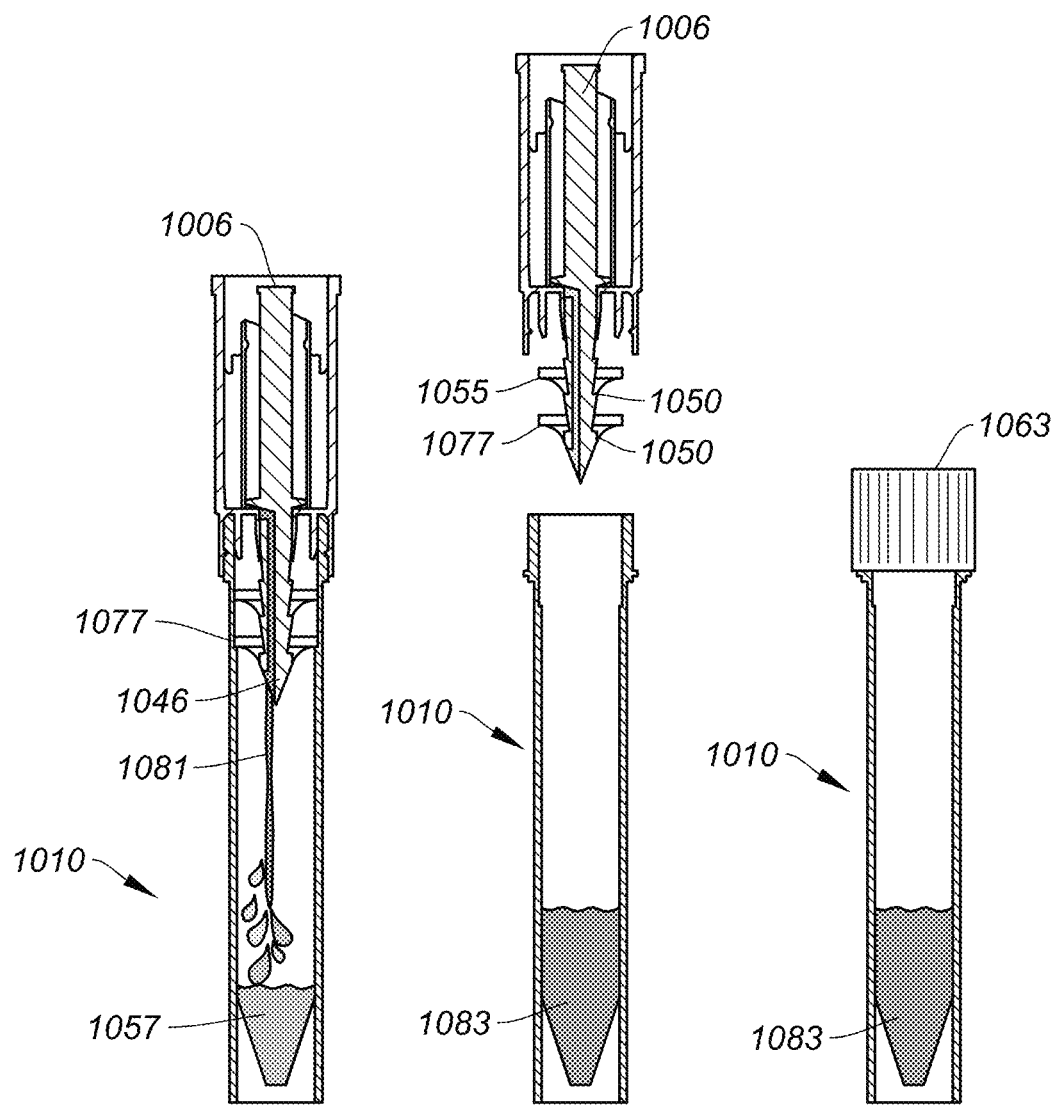

With reference to FIG. 27C, as the sample collection conduit 1006 is advanced further, the pointed end 1046 thereof breaks the first partition 1065. As a result, the first fluid 1079 which is the result of the mixing of the sample 1068 and the first reagent 1055, is able to mix with the second reagent 1075. With reference to FIG. 27D, as the sample collection conduit 1006 is advanced further, the pointed end 1046 also breaks, e.g. perforates, the second partition 1077. As a result, the second fluid 1081 which is a result of the mixture of the first reagent 1055, the sample 1068 and the second reagent 1075, is then able to flow towards the third reagent 1057.

Once all of the fluid has collected at the bottom of the sample analysis chamber 1010 the third fluid 1083 is the result of the mixture of the sample 1068 and each of the first, second and third reagents 1055, 1075, 1057. The sample collection part 1004 may be separated from the sample analysis chamber 1010 as shown in FIG. 27E. As depicted, the teeth 1050 on the sample collection conduit 1006 engage and hook onto the first and second partitions 1065, 1077, and thereby act to withdraw the first and second partitions 1065, 1077 from the sample analysis chamber 1010 when the sample collection part 1004 is separated therefrom.

With reference to FIG. 27F, a cap 1063 may be attached to the sample collection conduit 1010 so as to safely store the fluid 1083 therein. The fluid 1083 may then go on to be analyzed in the sample analysis chamber 1010 itself, or be dispensed therefrom for analysis, e.g onto/into a suitable analysis machine.

In the embodiments described above, the reagents may be any reagents which may be mixed with the sample. The reagents may also interact with the sample. The reagents may be in a solid or fluid, e.g. liquid, form. The reagents may comprise material which mixes with the sample, and/or comprise material which interacts with the sample, e.g. as part of a chemical or biological process.

Although the present invention has been described with reference to preferred embodiments, it will be understood by those skilled in the art that various changes in form and detail may be made without departing from the scope of the invention as set forth in the accompanying claims.

What is claimed is:

1. A sample collection device, for collecting a fluid sample, comprising:
   a sample collection chamber, for collecting a sample therein, having a first end and a second end;
   a sample collection conduit, for conveying a sample from a user into the sample collection chamber, wherein the sample collection conduit comprises an inlet for receiving a sample and wherein in at least a first position the sample collection conduit extends from within the sample collection chamber out through the first end of the sample collection chamber such that at least the inlet of the sample collection conduit is disposed outside of the sample collection chamber;
   a plunger configured to expel the sample out of the sample collection chamber through the second end of the sample collection chamber; and
   a seal arranged to close the second end of the sample collection chamber, and wherein the sample collection conduit and/or the plunger is configured to break the seal when moved towards a second position in which the sample collection conduit is moved into the sample collection chamber.

2. The sample collection device as claimed in claim 1, wherein the sample collection conduit and plunger are operatively linked such that movement of the sample collection conduit causes movement of the plunger.

3. The collection device as claimed in claim 1, wherein the sample collection chamber comprises at least one volumetric marking.

4. The sample collection device as claimed in claim 1, wherein the sample collection chamber comprises an air vent arranged to allow air to escape the sample collection chamber.

5. The sample collection device as claimed in claim 1, further comprising a flow redirection chamber, arranged at the second end of the sample collection chamber, and wherein when in the first position the sample collection conduit extends into the flow redirection chamber, and wherein the sample collection conduit comprises a first conduit in fluid connection with the inlet of the sample collection conduit and the flow redirection chamber and a second conduit in fluid communication with the flow redirection chamber and the sample collection chamber, such that fluid can flow from the inlet through the first conduit, via the flow redirection chamber and into the sample collection chamber.

6. The sample collection device as claimed in claim 1, comprising a restriction arrangement configured to prevent the sample collection conduit and/or the plunger from being retracted from the sample collection device as the sample collection conduit and/or the plunger is moved into the sample collection chamber.

7. The sample collection device as claimed in claim 1, further comprising a guide arrangement configured to prevent the sample collection conduit and/or plunger from rotating within the sample collection device for at least part of the range of linear movement of the sample collection conduit and/or plunger within the sample collection device.

8. The sample collection device as claimed in claim 1, further comprising a first position fixing means for holding the sample collection conduit in the first position.

9. The sample collection device as claimed in claim 1, further comprising an intermediate position fixing means for holding the sample collection conduit in an intermediate position, wherein in the intermediate position the plunger is positioned to close off an air vent in the sample collection chamber.

10. The sample collection device as claimed in claim 1, further comprising a second position fixing means for holding the sample collection conduit in a second position, in which the inlet of the sample collection conduit is contained within the sample collection device.

11. The sample collection device as claimed in claim 1, further comprising an overspill chamber, arranged to collect any sample which overspills the sample collection chamber.

12. The sample collection device as claimed in claim 1, further comprising a conduit seal arranged outside and below the second end of the sample collection chamber, and wherein the sample collection conduit is configured to come into contact with the conduit seal so as to seal an outlet of the sample collection conduit, when the sample collection conduit is moved into a second position in which the sample collection conduit extends through the second end of the sample collection chamber.

13. The sample collection device as claimed in claim 1, further comprising a cap arranged to close the sample collection chamber.

14. The sample collection device of claim 1, further comprising a connection arrangement for connecting a further component to the device.

15. The sample collection device of claim 1, further comprising a storage cap for attaching to the second end of the sample collection chamber.

16. The sample collection device as claimed in claim 1, further comprising a conduit cap configured to push the sample collection conduit into the sample collection chamber.

17. The sample collection device of claim 1, further comprising a sample analysis chamber configured to be connected to the second end of the sample collection chamber, for receiving the sample expelled from the sample collection chamber.

18. The sample collection device of claim 17, wherein the sample analysis chamber comprises at least one reagent arranged therein.

19. The sample collection device of claim 18, wherein the at least one reagent is contained within at least one capsule arranged within the sample analysis chamber.

20. A sample collection device, for collecting a fluid sample, comprising:
   a sample collection chamber, for collecting a sample therein, having a first end and a second end;
   a sample collection conduit, for conveying a sample from a user into the sample collection chamber, wherein the sample collection conduit comprises an inlet for receiving a sample and wherein in at least a first position the sample collection conduit extends from within the sample collection chamber out through the first end of the sample collection chamber such that at least the inlet of the sample collection conduit is disposed outside of the sample collection chamber;
   a plunger configured to expel the sample out of the sample collection chamber through the second end of the sample collection chamber; and
   a second position fixing means for holding the sample collection conduit in a second position, in which the inlet of the sample collection conduit is contained within the sample collection device.

* * * * *